(12) United States Patent
Kimura

(10) Patent No.: US 6,232,774 B1
(45) Date of Patent: May 15, 2001

(54) METHOD AND APPARATUS FOR MEASURING INTERNAL STRUCTURE OF A TARGET MAGNETIC BODY USING INDUCTANCE

(75) Inventor: Takashi Kimura, Nagoya (JP)

(73) Assignee: Magnegraph Co., Ltd., Aichi-Ken (JP)

( * ) Notice: Subject to any disclaimer, the term of this patent is extended or adjusted under 35 U.S.C. 154(b) by 0 days.

(21) Appl. No.: 09/233,854

(22) Filed: Jan. 19, 1999

(51) Int. Cl.[7] .................................................. G01N 27/72
(52) U.S. Cl. .......................... 324/235; 324/240; 324/232
(58) Field of Search .................................... 324/235, 225, 324/232, 233, 329, 240, 207.16, 207.17

(56) References Cited

U.S. PATENT DOCUMENTS

| | | | | |
|---|---|---|---|---|
| 3,707,672 | * | 12/1972 | Miller et al. | 324/239 |
| 4,503,392 | * | 3/1985 | Fastritsky et al. | 324/232 |
| 5,747,989 | * | 5/1998 | Kimura et al. | 324/235 |
| 6,037,768 | * | 3/2000 | Moulder et al. | 324/225 |

FOREIGN PATENT DOCUMENTS 3011090   8/1995 (JP).

* cited by examiner

Primary Examiner—Christine K. Oda
Assistant Examiner—Subhash Zaveri
(74) Attorney, Agent, or Firm—Beyer Weaver & Thomas, LLP

(57) ABSTRACT

The process first applies a magnetostatic field to a target magnetic body to magnetize the target magnetic body. The process then cuts the magnetostatic field off and measures a transient variation in a differential magnetic flux density at a plurality of positions in the vicinity of the target magnetic body. The process subsequently determines a time constant of the transient variation in the differential magnetic flux density at the plurality of positions. The process then determines a specific characteristic value relating to the internal structure of the target magnetic body, based on a distribution of the time constant over the plurality of positions. This arrangement enables a variety of internal structures of the target magnetic body to be examined in a non-destructive manner.

17 Claims, 19 Drawing Sheets

MODEL REPRESENTING PROCESS OF DISAPPEARANCE OF REMANENCE

EQUIVALENT CIRCUIT $\phi_1$ : MAGNETIC FLUX DENSITY $L_2$ : INDUCTANCE OF MAGNETIZED SPACE IN WHICH EDDY CURRENT IS GENERATED $R_2$ : ELECTRICAL RESISTANCE OF LOOP THROUGH WHICH EDDY CURRENT PASSES $i_2$ : EDDY CURRENT

M : INDUCTION COEFFICIENT

Fig. 3

EQUIVALENT CIRCUIT

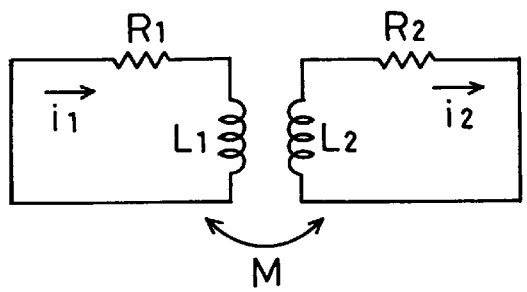

$L_1$ : INDUCTANCE OF MAGNETIC CIRCUIT
(VOLUME OF WHOLE MAGNETIC FLUX SPACE HAVING MAGNETIC FLUX)

$R_1$ : RESISTANCE TO THE CHANGE OF GIVEN MAGNETIC FLUX IN WHOLE MAGNETIC FLUX SPACE HAVING MAGNETIC FLUX $i_1$ : MAGNETIC FLUX DENSITY ($=\phi_1$)

$L_2$ : VOLUME OF MAGNETIZED SPACE IN WHICH EDDY CURRENT IS GENERATED $R_2$ : ELECTRICAL RESISTANCE OF LOOP THROUGH WHICH EDDY CURRENT PASSES $i_2$ : EDDY CURRENT

M : INDUCTION COEFFICIENT

INITIAL CONDITION t=0 (CUT OFF OF MAGNETOSTATIC FIELD), $i_1=I_0$, $i_2=0$

Fig. 5(a)

MAGNETIC FLUX DENSITY $i_1$

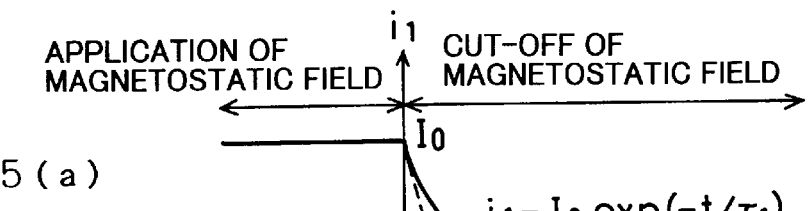

Fig. 5(b)

DIFFERENTIAL MAGNETIC FLUX DENSITY $\frac{di_1}{dt}$

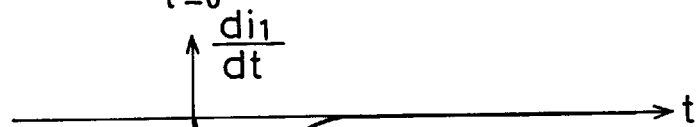

$$\frac{di_1}{dt} = f_1(t) + f_2(t)$$
$$= -\frac{I_0}{\tau_1}\exp(-t/\tau_1) + \frac{I_0}{\tau_1}\exp(-t/\tau_2)$$

Fig. 5(c)

ATTENUATION CHARACTERISTIC OF MAGNETIC ENERGY $f_1(t)$

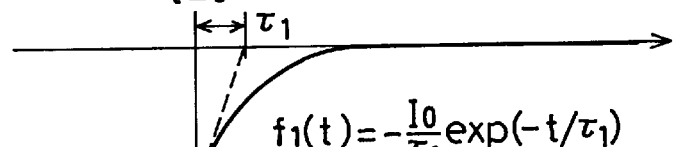

$$f_1(t) = -\frac{I_0}{\tau_1}\exp(-t/\tau_1)$$

Fig. 5(d)

ATTENUATION CHARACTERISTIC OF EDDY CURRENT LOSS $f_2(t)$

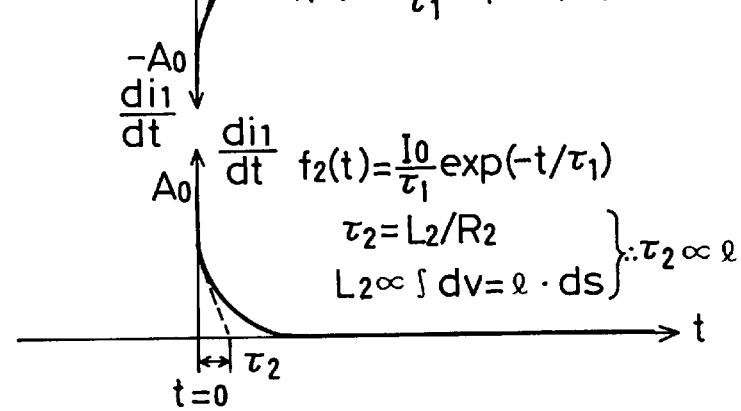

$$f_2(t) = \frac{I_0}{\tau_1}\exp(-t/\tau_1)$$
$$\left.\begin{array}{l}\tau_2 = L_2/R_2 \\ L_2 \propto \int dv = \ell \cdot ds\end{array}\right\} \therefore \tau_2 \propto \ell$$

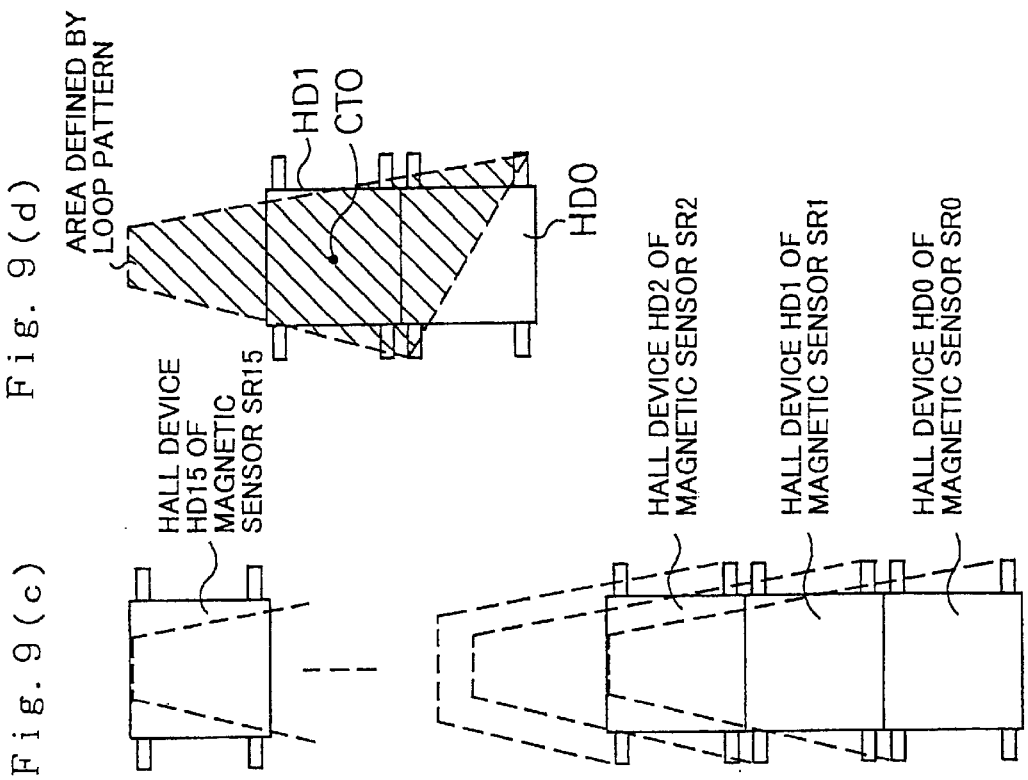
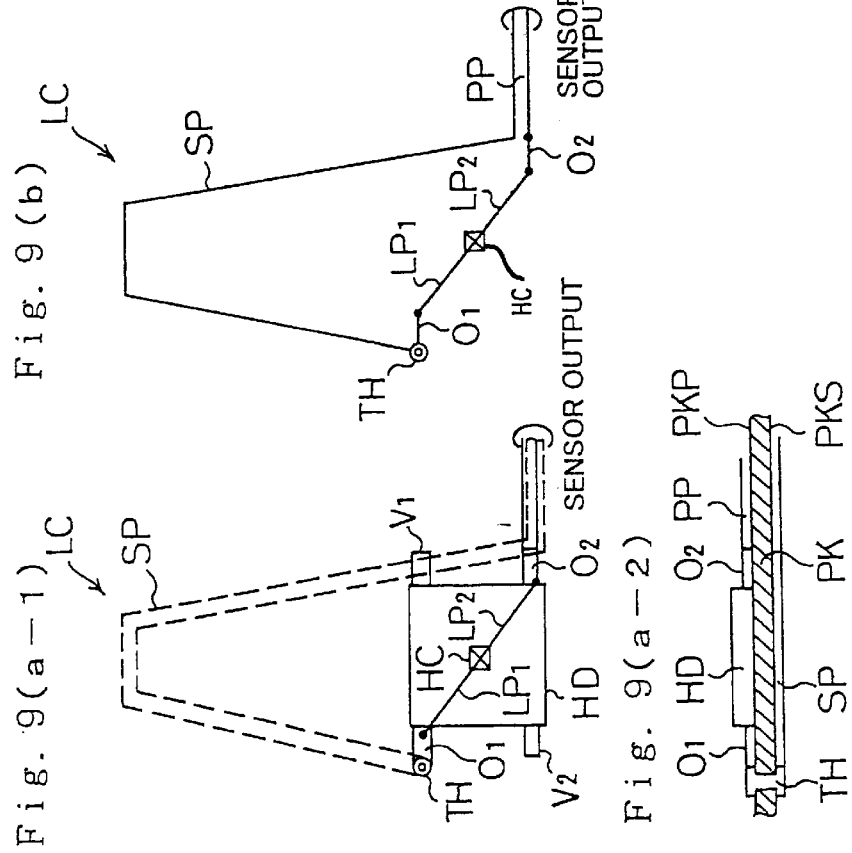

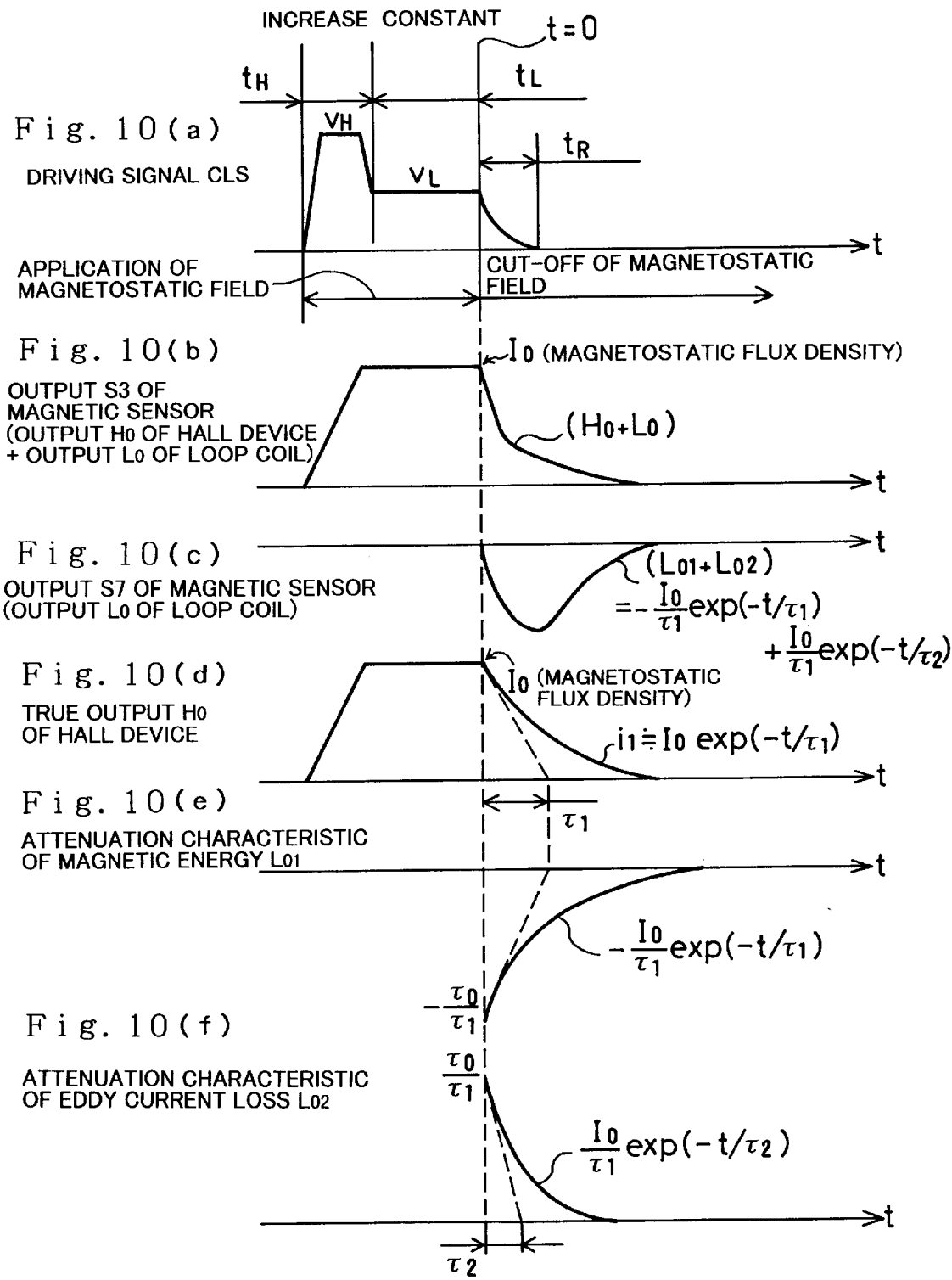

PROCESS OF MEASURING VARIATION IN MAGNETIC FLUX

[MAGNETOSTATIC FLUX DENSITY]
(INDENTATION)

[ATTENUATION CHARACTERISTIC OF EDDY CURRENT LOSS]
(JOINT PART)

[ATTENUATION CHARACTERISTIC OF MAGNETIC ENERGY]
(NUGGET)

POSITION OF SENSOR

METHOD AND APPARATUS FOR MEASURING INTERNAL STRUCTURE OF A TARGET MAGNETIC BODY USING INDUCTANCE

BACKGROUND OF THE INVENTION

1. Field of the Invention

The present invention relates to a method of examining an internal structure, such as a welding state and an internal defect, of a magnetic body like a steel plate in a non-destructive manner, as well as to an apparatus for the same.

2. Description of the Related Art

Spot welding is generally used in the automobile industry and for assembly of various metal thin plate products. The typical procedure of spot welding pinches layers of a metal base material between the appropriately formed ends of electrodes. The process then concentrates the electric current and the pressing force on a relatively narrow portion and thereby locally heat the relatively narrow portion, while applying the pressure to the relatively narrow portion with the electrodes. This is a sort of resistance welding.

The spot welded part generally has a sectional structure shown in FIG. 19. The surface of the welded part is concaved (indentation) by the pressure to be lower than the surrounding non-welded part. The dimension of the indentation is referred to as the indentation diameter. The welded part includes a nugget (deposit), which is the center of the welded part, and a circumferential contact-bonded portion. The nugget is formed by solidification of the fused metal. The contact-bonded portion is formed by bonding of the surfaces of the metal layers which are in closed contact with each other. The dimension of the nugget is referred to as the nugget diameter. The dimension of the sum of the nugget and the contact-bonded portion (that is, the actually joint part) is referred to as the joint diameter. Since the spot welding welds the layers of the metal base material at one point, it is often followed by an examination to check whether the welding strength is sufficient or not.

One effective method of measuring the welding strength in a non-destructive manner measures the nugget (deposit) diameter of the welded part to determine the welded strength. A known method of measuring the nugget diameter applies an ac magnetic field, which is produced by a coil through which a high-frequency electric current flows, to the spot welded part and measures a resulting variation in inductance of the coil to determine the nugget diameter. The conventional method takes advantage of the characteristic that the permeability is different between the nugget and the non-nugget portion, and observes a variation in permeability as a variation in inductance to determine the nugget diameter.

The indentation has a less thickness, and the indentation diameter thereby affects the structural strength. The nugget diameter and the joint diameter, on the other hand, affect the joint strength. In order to determine the welding strength of the spot welded part with high accuracy, it is desirable to determine all the indentation diameter, the nugget diameter, and the joint diameter.

The conventional method, however, measures only the nugget diameter and does not determine the other structural characteristic values, such as the indentation diameter and the joint diameter. There has been a strong demand or the technique that measures a variety of internal structures of not only the spot welded part but a general magnetic body in a non-destructive manner.

SUMMARY OF THE INVENTION

The object of the present invention is thus to provide a method of measuring a variety of internal structures of a magnetic body in a non-destructive manner and an apparatus for the same.

At least part of the above and the other related objects is attained by a method of examining an internal structure of a target magnetic body, the method comprising the steps of: (a) applying a magnetostatic field to a target magnetic body to magnetize the target magnetic body; (b) cutting the magnetostatic field off and subsequently measuring a transient variation in a differential magnetic flux density at a plurality of positions in the vicinity of the target magnetic body; (c) determining a time constant of the transient variation in the differential magnetic flux density at the plurality of positions; and (d) determining a specific characteristic value relating to the internal structure of the target magnetic body, based on a distribution of the time constant over the plurality of positions.

The term 'internal structure' is used here in a wide sense that includes not only a mechanical structure but magnetic properties, a chemical composition, and the like.

The time constant of the transient variation in differential magnetic flux density is affected by the inductance of a space having a magnetic field and the degree of resistance to the change of a given magnetic flux in the space having the magnetic flux, as well as by the inductance of the internal portion of the magnetic body, through which the magnetic flux passes, and the electrical resistance of the magnetic body. The inductance of a space having a magnetic field, the degree of resistance to the change of a given magnetic flux in the space having the magnetic flux, the inductance of an internal portion of the magnetic body through which the magnetic flux passes, and the electrical resistance of the magnetic body have distributions reflecting the internal structure of the magnetic body. The method of the present invention can thus specify the internal structure of the magnetic body, based on a change of the time constant of the transient variation in differential magnetic flux density. This arrangement enables a variety of internal structures of the magnetic body to be measured in a non-destructive manner.

In accordance with one preferable application of the method, the step (c) includes the step of: assuming the transient variation in the differential magnetic flux density to be a combination of a transient variation in a first differential magnetic flux density corresponding to an attenuation of a first magnetic flux density caused by the magnetostatic field and a transient variation in a second differential magnetic flux density corresponding to an attenuation of a second magnetic flux density caused by an eddy current, which is induced by the attenuation of the first magnetic flux density, and determining at least one of a first time constant defining the transient variation in the first differential magnetic flux density and a second time constant defining the transient variation in the second differential magnetic flux density.

The first time constant and the second time constant are related to different characteristic values, which respectively represent internal structures of the target magnetic body. This means that the different characteristic values, which represent the different internal structures of the target magnetic body, are specified from the first time constant and the second time constant.

In accordance with one preferable structure of the method, the target magnetic body is a plate assembly obtained by joining two metal plates by spot welding, and the step (d) includes the step of: determining a shape of a nugget portion of a spot welded part, based on a distribution of the first time constant.

The nugget portion of the spot welded part experienced a change of the metal configuration during the welding. The first time constant is varied with the change in the chemical composition inside the magnetic body. The shape of the nugget portion can thus be specified from the distribution of the first time constant.

In accordance with another preferable structure of the method, the target magnetic body is a plate assembly obtained by joining two metal plates by spot welding, and the step (d) includes the step of: determining a shape of a joint portion of a spot welded part, based on a distribution of the second time constant.

The magnetic path of the magnetic flux changes at a certain position in the vicinity of a joint end (that is, a boundary of the joint portion) and outside the joint portion of the spot welded part. Concretely, the magnetic path of the magnetic flux goes around the side of the joint portion. There is accordingly a position where the magnetic path length of the magnetic flux abruptly changes (a point of change of the magnetic path length). The second time constant depends on the change in the magnetic path length of the magnetic flux that passes through the target magnetic body. Determining a change of the second time constant results in determining the point of change of the magnetic path length and thereby specifying the shape of the joint portion.

The present invention is also directed to an apparatus for examining an internal structure of a target magnetic body. The apparatus includes: a magnetostatic field application unit that applies a magnetostatic field to a target magnetic body to magnetize the target magnetic body; a measurement unit that cuts the magnetostatic field off and subsequently measures a transient variation in a differential magnetic flux density at a plurality of positions in the vicinity of the target magnetic body; a time constant determination unit that determines a time constant of the transient variation in the differential magnetic flux density at the plurality of positions; and a structural characteristic determination unit that determines a specific characteristic value relating to the internal structure of the target magnetic body, based on a distribution of the time constant over the plurality of positions.

The apparatus of the present invention has the same functions and effects as those of the method discussed above. The apparatus of the present invention can thus specify the internal structure of the magnetic body, based on a change of the time constant of the transient variation in the differential magnetic flux density. This arrangement enables a variety of internal structures of the magnetic body to be measured in a non-destructive manner.

BRIEF DESCRIPTION OF THE DRAWINGS

FIG. 3 shows a magnetic equivalent circuit that replaces the closed loop of the magnetic flux density $\phi_1$ shown in FIG. 2(*b*);

FIGS. 5(*a*) through 5(*d*) show variations of the magnetic flux observed with the array sensor SR;

FIGS. 9(*a*-1) through 9(*d*) show an exemplified structure of the array sensor 12;

FIGS. 10(*a*) through 10(*f*) show the outputs of a magnetic sensor and results of data processing;

DESCRIPTION OF THE PREFERRED EMBODIMENTS

The following describes a method of and an apparatus for determining a nugget diameter and a joint diameter of spot welding as an embodiment according to the present invention. The embodiment regards a steel plate, which is an example of the magnetic body having electrical conductivity, as the target of measurement.

A. Principle of Measurement

Figure 1A:
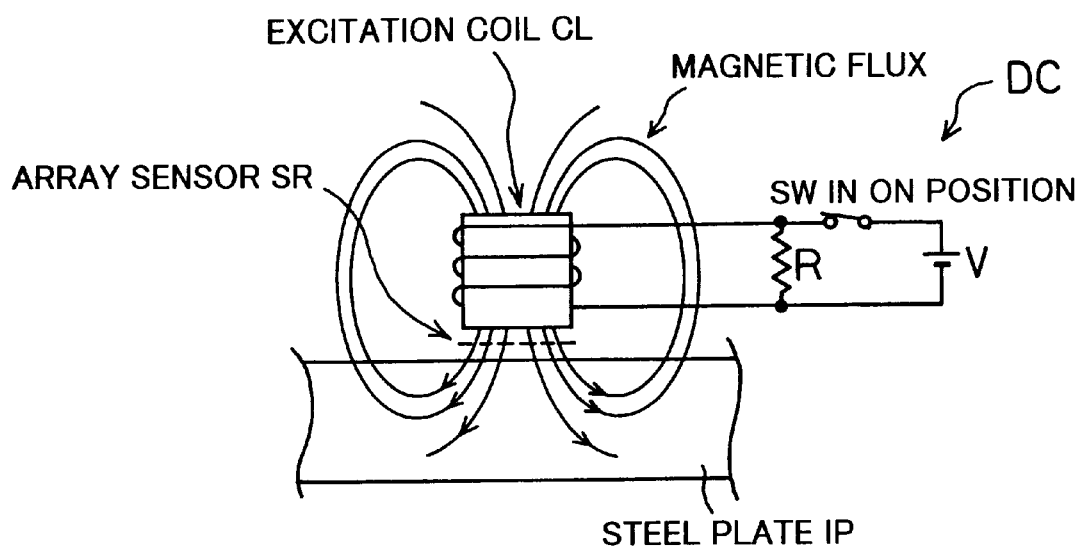
FIGS. 1(*a*) and 1(*b*) schematically illustrate the structure and operations of a measurement apparatus in an embodiment of the present invention.

FIGS. 1(*a*) and 1(*b*) schematically illustrate the structure and operations of a measurement apparatus in the embodiment of the present invention. The measurement apparatus includes an excitation coil CL, an excitation coil-driving circuit DC (including a voltage source V, a switch SW, and a resistance R), and an array sensor SR (including a plurality of magnetism-sensitive elements) that measures a variation in magnetic flux density in the vicinity of a steel plate IP. The measurement apparatus applies a magnetostatic filed to the steel plate IP and then cuts the magnetostatic field off, in order to measure a variation in magnetic flux density after the cut-off with the array sensor SR.

Figure 1B:
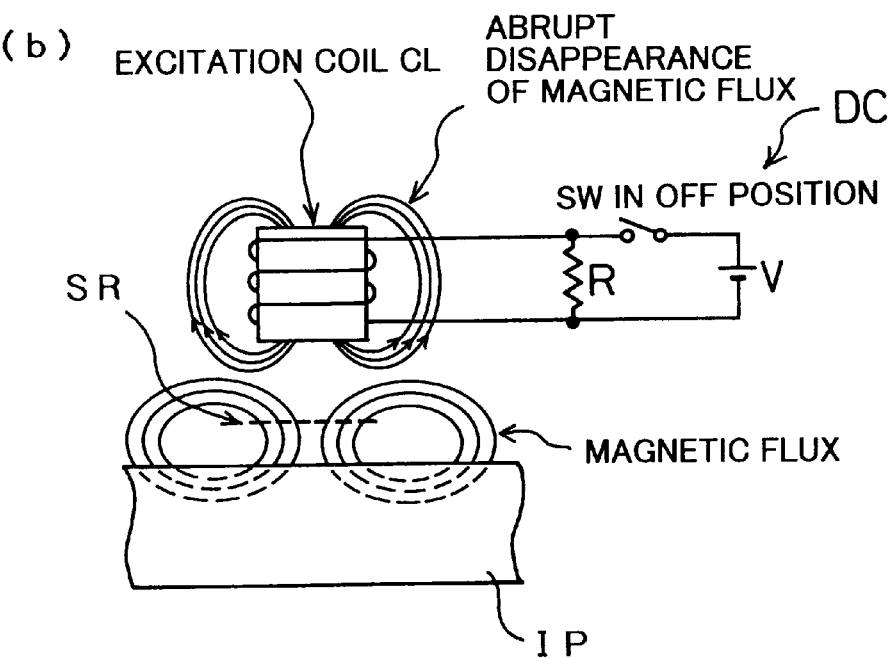

FIG. 1(*a*) shows the state in which the switch SW is in the ON position to apply a voltage output from the voltage source V to the excitation coil CL and thereby apply a magnetostatic field to the steel plate IP. The portion of the steel plate IP, through which the magnetic flux passes, is magnetized according to the intensity of the magnetostatic field. FIG. 1(b) shows the state in which the switch SW is in the OFF position to cut the magnetostatic field off. In this state, the loop of the magnetic flux is divided into a closed loop in the vicinity of the excitation coil CL and a closed loop in the vicinity of the steel plate IP. The closed loop of the magnetic flux in the vicinity of the excitation coil CL abruptly decreases and disappears. The closed loop of the magnetic field in the vicinity of the steel plate IP, on the other hand, does not disappear immediately (remanence), but is kept as magnetic energy in the magnetic body. The closed loop of the magnetic field then gradually decreases, and the state of the steel plate IP is eventually returned to the conditions before the application of the magnetostatic field.

The array sensor SR located in the vicinity of the surface of the steel plate IP measures a variation in magnetic flux in the vicinity of the steel plate IP. It is supposed in the ideal state that the variation in magnetic flux observed by the array sensor SR after the cut-off of the magnetostatic field decreases exponentially in a monotonous manner. In the actual state, however, the presence of a loss makes the variation in magnetic flux deviated from the ideal curve. It is thought that the loss is caused by the occurrence of eddy currents induced by a variation in magnetization in the steel plate IP in the course of disappearance of the magnetic energy stored in the steel plate IP. In this embodiment, a model discussed below is assumed as the model that gives a variation in magnetic flux after the cut-off of the magnetostatic field.

Figure 2A:
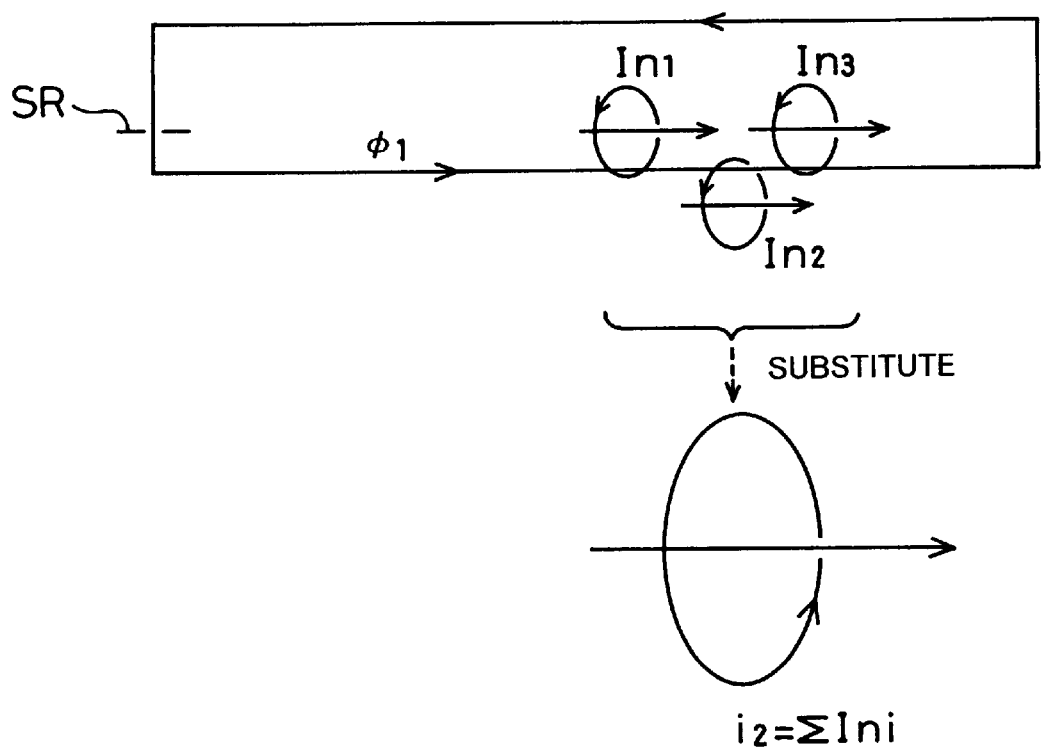
FIGS. 2(*a*) and 2(*b*) show a model representing a process of disappearance of the remanence and its equivalent circuit.
Figure 2B:
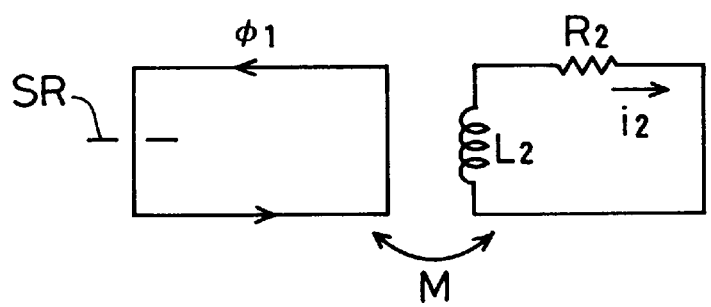

FIGS. 2(a) and 2(b) show a model representing a process of disappearance of the remanence and its equivalent circuit. In FIG. 2(a), $\phi_1$ denotes a magnetic flux density that passes through an arbitrary magnetism-sensitive element included in the array sensor SR in the process of the disappearance of the magnetic energy. $I_{n_1}, I_{n_2}, I_{n_3}, \ldots$ represent eddy currents induced by a variation in magnetic flux density $\phi_1$, and $M_1, M_2, M_3, \ldots$ denote induction coefficients of the eddy currents. It is assume that the eddy currents $I_{n_1}, I_{n_2}, I_{n_3}, \ldots$ induced by the variation in magnetic flux density $\phi_1$ are independent of one another. Upon such assumption, the eddy currents $I_{n_1}, I_{n_2}, I_{n_3}, \ldots$ are replaced by one eddy current $i_2$ induced by an induction coefficient $M=\Sigma M_i$ ($i=1, 2, 3, \ldots$) according to the variation in magnetic flux density $\phi_1$. The process of the disappearance of the magnetic flux that passes through one arbitrary magnetism-sensitive element included in the array sensor SR is accordingly expressed by the magnetic flux density $\phi_1$ and the eddy current $i_2$ which is induced by the magnetic flux density $\phi_1$ with the induction coefficient M. FIG. 2(b) shows an equivalent circuit of FIG. 2(a), where $R_2$ denotes an electrical resistance of the eddy current $i_2$ and $L_2$ denotes an inductance of the ddy current $i_2$.

FIG. 3 shows a magnetic equivalent circuit that replaces the closed loop of the magnetic flux density $\phi_1$ shown in FIG. 2(b), where $R_1$ denotes a resistance to the change of a given magnetic flux, $L_1$ denotes an inductance of the magnetic circuit, and $i_1$ denotes a magnetic flux density (corresponding to $\phi_1$ in FIGS. 2(a) and 2(b)). The induction coefficient M has the significance of a mutual inductance between the inductance $L_1$ of the magnetic circuit and the inductance $L_2$ of the eddy current circuit.

Figure 4:
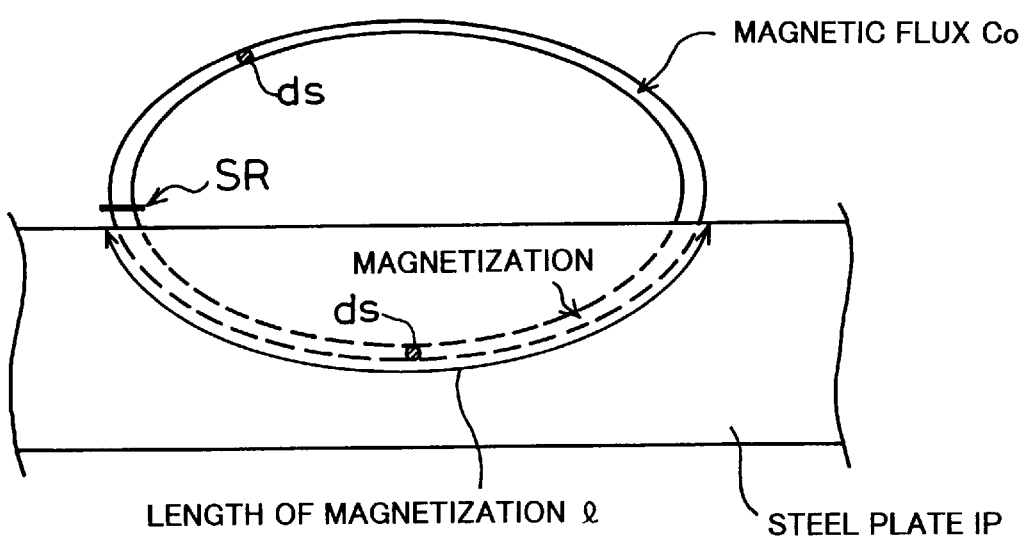
FIG. 4 shows a closed loop $C_0$ of the magnetic flux $i_1$ (=$\phi_1$) passing through one arbitrary magnetism-sensitive element included in the array sensor SR immediately after the cut-off of the magnetostatic field.

The inductance $L_1$ of the magnetic circuit corresponds to the volume of a whole magnetic flux space having the magnetic flux density $i_1$ as discussed below. FIG. 4 shows a closed loop $C_0$ of the magnetic flux $i_1$ ($=\phi_1$) passing through one arbitrary magnetism-sensitive element included in the array sensor SR immediately after the cut-off of the magnetostatic field. The magnetic energy stored during the application of the magnetostatic field does not disappear immediately but decreases gradually. It is thought that the magnetic energy is kept in the closed loop space of the magnetic flux and gradually decreases according to the resistance to the change of the given magnetic flux in the space. The magnetic energy W is expressed by Equation (1) given below:

$$W = \frac{1}{2}\int i_1^2 dv = \frac{1}{2}L \cdot i_1^2 \tag{1}$$

where L denotes a value that is proportional to the volume of the space having the magnetic flux (that is, the space having the magnetic energy). Equation (1) is identical with the equation that determines the energy stored during the flow of the electric current $i_1$ through the coil of the inductance L. The inductance $L_1$ shown in FIG. 3 accordingly corresponds to the volume of the whole space having the magnetic flux.

The equivalent circuit shown in FIG. 3 is expressed by Equations (2) given below:

$$L_1 \frac{di_1}{dt} + R_1 i_1 - M\frac{di_2}{dt} = 0 \tag{2}$$

$$L_2 \frac{di_2}{dt} + R_1 i_2 - M\frac{di_1}{dt} = 0$$

Equations (2) are rewritten as Equations (3a) nad (3b) given below:

$$i_1 = A_1 \exp(-(\alpha-\gamma)t) - A_2 \exp(-(\alpha+\gamma)t) \tag{3a}$$

$$i_2 = B_1 \exp(-(\alpha-\gamma)t) - B_2 \exp(-(\alpha+\gamma)t) \tag{3b}$$

$$\alpha = \frac{L_1 R_2 + L_2 R_1}{2(L_1 L_2 - M^2)}$$

$$\gamma = \frac{\sqrt{(L_1 R_2 - L_2 R_1)^2 - 4R_1 R_2 M^2}}{2(L_1 L_2 - M^2)}$$

$$A_1 = \frac{-(L_1 R_2 - L_2 R_1) - \sqrt{(L_1 R_2 - L_2 R_1)^2 + 4R_1 R_2 M^2}}{2R_1\sqrt{(L_1 R_2 - L_2 R_1)^2 + 4R_1 R_2 M^2}}$$

$$A_2 = \frac{(L_1 R_2 - L_2 R_1) - \sqrt{(L_1 R_2 - L_2 R_1)^2 + 4R_1 R_2 M^2}}{2R_1\sqrt{(L_1 R_2 - L_2 R_1)^2 + 4R_1 R_2 M^2}}$$

$$B_1 = \frac{-M}{\sqrt{(L_1 R_2 - L_2 R_1)^2 + 4R_1 R_2 M^2}}$$

$$B_2 = B_1$$

The constants in Equations (3a) and (3b) are determined on the assumption that the magnetic flux density $i_1$ at the time of the cut-off of the magnetostatic field (t=0) is set equal to $I_0$ as an initial condition. The following results are obtained when the induction coefficient M is sufficiently small and the eddy current $i_2$ induced by the variation in magnetic flux density $i_1$ is sufficiently small, that is, when $L_1 \cdot L_2 >> M \cdot M$:

$$\alpha - \gamma \approx \frac{R_1}{L_1} = \frac{1}{\tau_1} \tag{4a}$$

$$\alpha + \gamma \approx \frac{R_2}{L_2} = \frac{1}{\tau_2} \tag{4b}$$

-continued $$A_1 \approx I_0 \approx -\frac{1}{R_1} \qquad (4c)$$

$$A_2 \approx 0 \qquad (4d)$$

$$B_1 \approx 0 \qquad (4e)$$

$$B_2 \approx 0 \qquad (4f)$$

Substituting Approximation Equations (4a) and (4b) into Equation (3a) gives Equation (5) shown below:

$$i_1 = A_1 \exp(-t/\tau_1) - A_2 \exp(-t/\tau_2) \qquad (5)$$

The actually observed value is the magnetic flux density $i_1$ in the left-hand side of Equation (5). The graph of FIG. 5(a) shows a transient variation in magnetic flux density $i_1$ defined by Equation (5). As clearly understood by Equation (4d), the second term in the right-hand side of Equation (5) is negligible, and Equation (5) can be approximated by only the first term in the right-hand side. The voltage observed in a loop coil, which is generally used as a magnetic sensor, is proportional to a variation ratio of the magnetic flux density, that is, a differential magnetic flux density. By differentiating Equation (5) by the time t, Equation (6) is obtained as the equation of the differential magnetic flux density:

$$\begin{aligned}\frac{di_1}{dt} &= -\frac{A_1}{\tau_1}\exp(-t/\tau_1) + \frac{A_2}{\tau_2}\exp(-t/\tau_2) \qquad (6)\\ &= -\frac{A_1}{\tau_1}\left(\exp(-t/\tau_1) - \frac{A_2\tau_1}{A_1\tau_2}\exp(-t/\tau_2)\right)\\ &\quad \left(t=0, \frac{di_1}{dt} = 0 \rightarrow \frac{A_2\tau_1}{A_1\tau_2} = 1\right)\\ &= -\frac{A_1}{\tau_1}(\exp(-t/\tau_1) - \exp(-t/\tau_2)) \qquad (A_1 \approx I_0)\\ &= -\frac{I_0}{\tau_1}(\exp(-t/\tau_1) - \exp(-t/\tau_2))\end{aligned}$$

The graph of FIG. 5(b)) shows a transient variation in differential magnetic flux density given by Equation (6). The waveform of FIG. 5(b) substantially coincides with the result of actual measurement with a loop coil as the magnetic sensor. This indicates that the model discussed with FIGS. 2(a) through 4 correctly reflects the phenomenon. Equation (5) represents a variation in magnetic flux density $i_1$ observed with the sensor, and Equation (6) represents a variation in differential magnetic flux density ($di_1/dt$).

A time constant $\tau_1$ of the first term in the right-hand side of Equation (6) is equal to $L_1/R_1$ as given by Equation (4a). This term accordingly corresponds to the time constant of the magnetic circuit with the magnetic flux density $i_1$ shown in FIG. 3. The first term in the right-hand side of Equation (6) thus indicates an ideal monotonous decrease characteristic that represents an exponential decrease of the magnetic flux density in the vicinity of the steel plate IP after the cut-off of the magnetostatic field, that is, an attenuation characteristic of the magnetic energy (see the graph of FIG. 5(c)). It has been shown experimentally that a nugget portion, where the metal configuration has a change, and a non-nugget portion, where the metal configuration does not have a change, in a spot welded part have different values for the time constant $\tau_1$. Measurement and analysis of a distribution of the time constant $\tau_1$ in the spot welded part enables determination of the shape and size of a portion having a change in metal configuration, such as the nugget portion.

A time constant $\tau_2$ of the second term in the right-hand side of Equation (6) is equal to $L_2/R_2$ as given by Equation (4b). This term accordingly corresponds to the time constant of the equivalent circuit with the eddy current $i_2$ shown in FIG. 3. The second term in the right-hand side of Equation (6) thus represents an attenuation characteristic of the eddy current loss (see the graph of FIG. 5(d)). $R_2$ corresponds to the resistance of the eddy current (that is, the electrical resistance of the material), and $L_2$ corresponds to the volume of the magnetized space of the eddy current. As clearly understood from FIG. 4, $L_2$ is given by the following Expression (7):

$$L_2 \int du = l \cdot ds \qquad (7)$$

where l denotes the length of magnetization in the steel plate and ds denotes the magnetic flux-passing area.

According to Equation (4b) and Expression (7), the time constant $\tau_2$ of the attenuation characteristic of the eddy current loss is proportional to the magnetic path that generates the eddy current, that is, the length of the magnetic path passing through the steel plate, as shown by Expression (8) given below:

$$\tau_2 l \qquad (8)$$

A variation in magnetic path length of the magnetic flux passing through the vicinity of the spot welded part can accordingly be observed as a change of the time constant $\tau_2$ of the attenuation characteristic, which is the second term in the right-hand side of Equation (6).

Figure 6A:
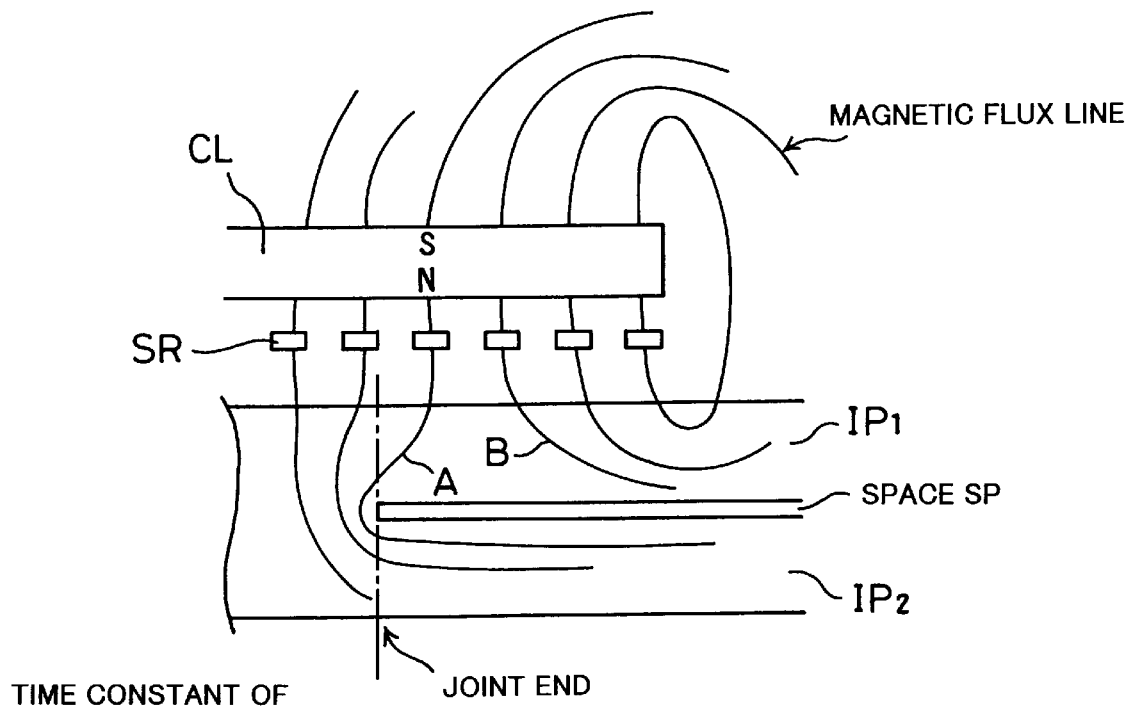
FIGS. 6(*a*) and 6(*b*) show the relationship between a state of the magnetic flux in the vicinity of a joint end of a spot welded part and a variation in time constant $\tau_2$ of the attenuation characteristic of eddy current loss.
Figure 6B:
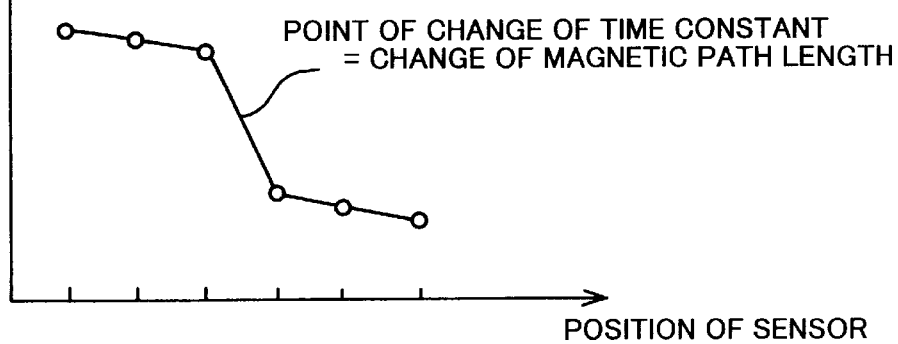

FIGS. 6(a) and 6(b) show the relationship between a state of the magnetic flux in the vicinity of a joint end of the spot welded part and a variation in time constant $\tau_2$ of the attenuation characteristic of eddy current loss. When a magnetic field is applied in the vicinity of a joint end of the spot welded part (that is, a boundary between the joint portion and the space), the magnetic flux is in the state shown in FIG. 6(a). Under such conditions, the magnetic path of the magnetic flux abruptly changes and branches off to left and right paths at a certain position in the vicinity of the joint end. A magnetic flux line B passes through an upper steel plate $IP_1$ above the space SP, whereas a magnetic flux line A goes around the joint portion and passes through a lower steel plate $IP_2$ below the space SP. The change is ascribed to the presence of the joint end. Specifying the position where the path of the magnetic flux abruptly changes enables estimation of the position of the joint end. The magnetic flux lines A and B have a difference in path of the magnetic flux, that is, a difference in magnetic path length. A plurality of sensors are located in the vicinity of the spot welded part of the steel plate, and the time constant $\tau_2$ is measured at each sensor position. A point of abrupt change of the time constant as shown in the graph of FIG. 6(b), that is, a point of abrupt change of the magnetic path length is then determined according to the results of the measurement. This results in estimating the joint end and the joint diameter of the spot welded part.

Based on the above description, the principles of measurement of the spot welded part are summarized to include:

(I) measuring transient variations in differential magnetic flux with a plurality of magnetic sensors arranged in the vicinity of a target body, which is an object to be measured and is, for example, a steel plate, after the magnetostatic field applied to the target body is cut off;

(II) determining the time constant $\tau_1$ of the attenuation characteristic of magnetic energy and the time constant $\tau_2$ of the attenuation characteristic of eddy current loss, based on the transient variations in differential magnetic flux density observed with the respective sensors;

(IIIa) determining a point of abrupt change of the time constant $\tau_1$ observed at the respective positions of the magnetic sensors, and estimating the shape of a portion having the varied metal configuration, such as the nugget portion; and (IIIb) determining a point of abrupt change of the time constant $\tau_2$ observed at the respective positions of the magnetic sensors, and estimating the shape of the joint portion.

B. Structure of Measurement Apparatus

Figure 7:
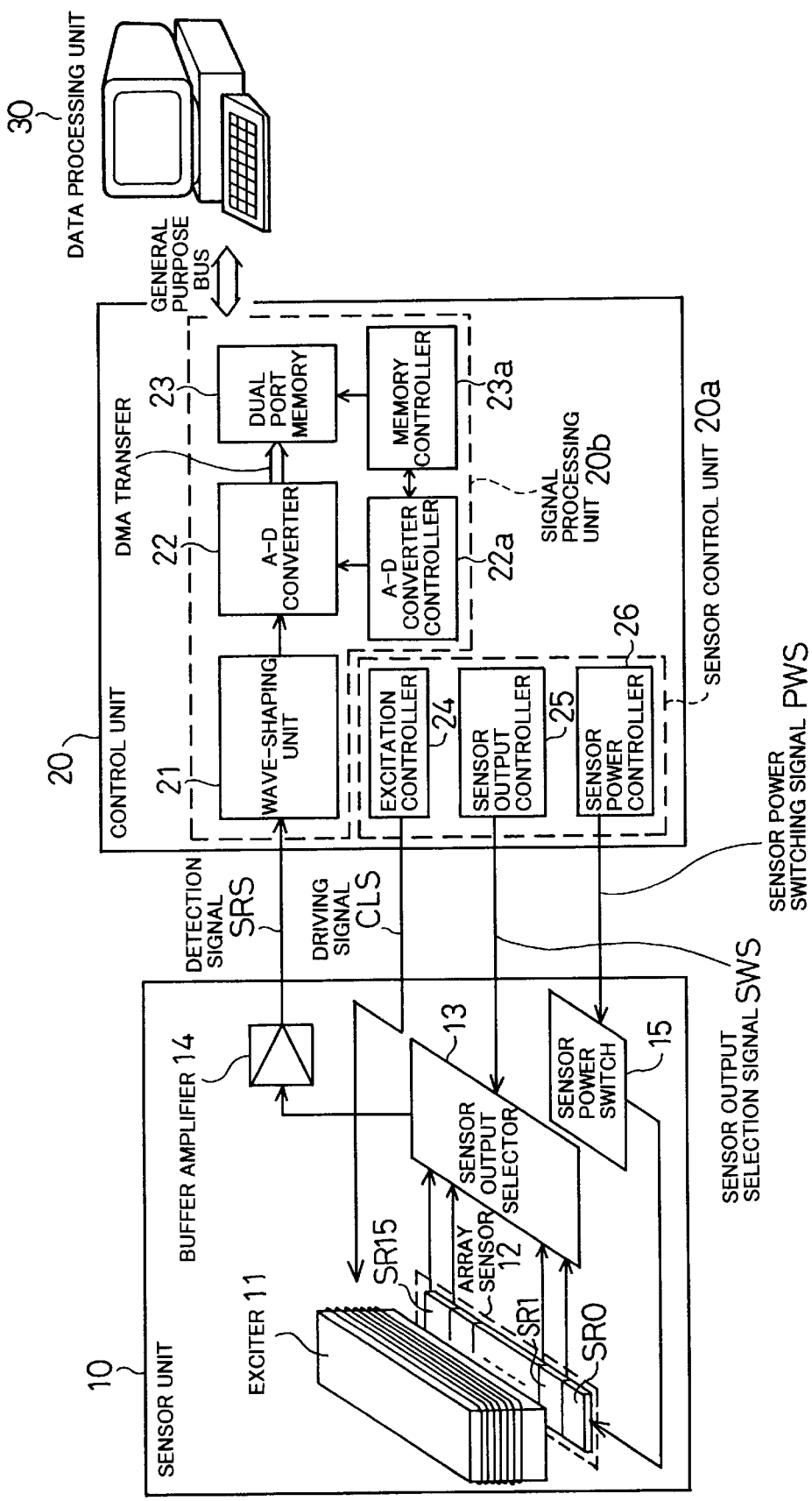
FIG. 7 is a block diagram illustrating the structure of a measurement apparatus that measures the welding state of the spot welded part of the steel plate.

FIG. 7 is a block diagram illustrating the structure of a measurement apparatus that takes advantage of the principles of measurement discussed above and examines the welding state (indentation diameter, nugget diameter, joint diameter) of the spot welded part of the steel plate. The measurement apparatus includes a sensor unit 10, a control unit 20, and a data processing unit 30. The data processing unit 30 is actualized, for example, by a conventional computer system. The control unit 20 is a control circuit connected to the data processing unit 30 via a general purpose bus and more specifically a control board inserted into a general purpose slot of the computer system.

Referring to FIG. 7, the sensor unit 10 has an exciter 11, an array sensor 12, a sensor output selector 13, a buffer amplifier 14, and a sensor power switch 15. The exciter 11 is an iron-cored excitation coil that applies and cuts off a magnetostatic field in response to a driving signal CLS output from the control unit 20. The array sensor 12 consists of sixteen magnetic sensors SR0 through SR15 that are aligned. The array sensor 12 is arranged immediately below the exciter 11 across a predetermined gap and along the longitudinal axis thereof The array sensor 12 detects a variation in magnetism in the vicinity of the target body during the application of the magnetostatic field and after the cut-off of the magnetostatic field, and outputs the result of detection as a variation in voltage. The sensor output selector 13 is a circuit that selects only one of the outputs of the respective magnetic sensors SR0 through SR15 included in the array sensor 12 and transmits the selected output to the buffer amplifier 14. The outputs of the respective magnetic sensors SR0 through SR15 are successively selected and transmitted in response to 4-bit sensor output selection signals SWS. The buffer amplifier 14 is a buffer circuit that supplies the output signal of the sensor output selector 13 as a detection signal SRS to the control unit 20. The sensor power switch 15 is a switching circuit that starts and cuts off the supply of power to the respective magnetic sensors SR0 through SR15 included in the array sensor 12. The circuits other than the array sensor 12 are generally known and may have any circuit structures that are easily actualized by those in the art.

Figure 8:
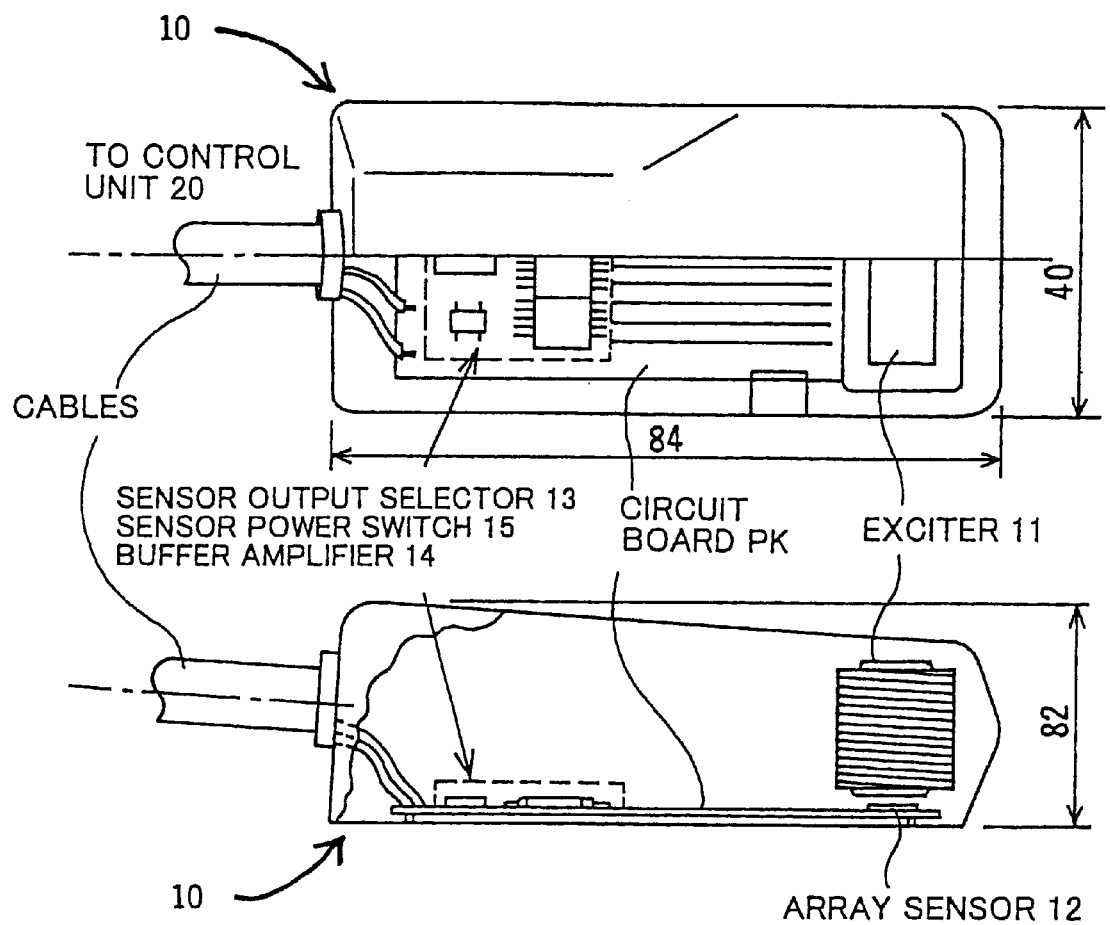
FIG. 8 shows an exemplified structure of the sensor unit 10.

FIG. 8 shows an exemplified structure of the sensor unit 10. The sensor unit 10 is mounted on a circuit board PK and is accommodated in a box-like casing having the length of 84 mm, the width of 40 mm, and the height of 82 mm. The sensor unit 10 is connected with the control unit 20 via a cable. This arrangement enables only the sensors to be in contact with the measurement positions of the target body and thereby effects the flexible measurement.

FIGS. 9($a$-1) through 9($d$) show an exemplified structure of the array sensor 12. FIGS. 9($a$-1) and 9($a$-2) schematically illustrate the structure of one magnetic sensor included in the array sensor 12. The magnetic sensor includes one Hall device HD mounted on a parts surface PKP of a circuit board $\overline{PK}$, a soldering pattern SP on a soldering surface PKS connected to an output terminal O1 of the Hall device HD via a through hole TH, and a parts surface pattern connected to another output terminal O2 of the Hall device HD. The pattern of the wiring forms a loop coil LC. Terminals V1 and V2 are power source terminals of the Hall device HD. As shown in FIG. 9($b$), the loop coil LC includes a lead wire OP2 connecting the output terminal O2 and a Hall chip HC, that is, a semiconductor chip of the Hall device HD, a lead wire LP1 connecting the Hall chip HC with the output terminal O1, and the soldering pattern SP connected with the output terminal O1 via the through hole TH and wired in a loop shape to the position immediately below the output terminal O2. The wiring pattern to the sensor output consists of the parts surface pattern PP and the soldering pattern SP. Wiring the parts surface pattern PP and the soldering pattern SP parallel to each other along the vertical axis protects the wiring pattern from being affected by the magnetic field. Since the loop coil LC is formed on the soldering surface PKS, the magnetic sensors, each including the Hall device HD and the loop coil LC, may be arranged at the intervals corresponding to the size of the Hall device HD as shown in FIG. 9($c$). A variation in differential magnetic flux density observed by the loop coil LC is practically regarded as a change at a center of gravity CTO of the hatched area defined by the loop pattern shown in FIG. 9($d$). The measurement position of the loop coil LC can be set by arbitrarily designing the shape of the loop coil LC.

FIG. 9($d$) shows an example, in which the center of gravity CTO of the loop coil LC included in the magnetic sensor SR0 is located on the center of the Hall device HD1 (that is, at the position where the Hall chip is mounted) of the adjacent magnetic sensor SR1. The center of gravity CTO of the loop coil LC may alternatively be located in the middle of the interval between the adjoining magnetic sensors. In the latter case, a variation in magnetism measured by the loop coil LC practically represents a variation in magnetism at the intermediate position of the adjoining Hall devices HD. By taking advantage of this fact, the interval between the adjoining magnetic sensors accordingly comes one half size of the interval between the adjoining Hall devices. This arrangement effectively improves the accuracy of measurement. In one possible modification, only the Hall devices may be used, and the differential magnetic flux density is calculated from the observed magnetic flux density. In another possible modification, only the loop coils may be used and the magnetic flux density is calculated from the observed voltage (differential magnetic flux density).

When the variation in magnetism is measured with the magnetic sensor shown in FIGS. 9($a$-1) through 9($d$), the structure of the magnetic sensor causes a detection signal of the loop coil to be added to a detection signal of the Hall device. In order to obtain the true detection signal of the Hall device, the procedure cuts off the power supply applied to the Hall device to inactivate the Hall device, measures only the output of the loop coil, and subtracts the output of the loop coil from the observed detection signal (Hall device+loop coil).

Referring back to FIG. 7, the control unit 20 includes a sensor control unit 20$a$ that controls the sensor unit 10 and a signal processing unit 20$b$ that converts the detection signals SRS to digital data. The sensor control unit 20$a$ includes an excitation controller 24, a sensor output controller 25, and a sensor power controller 26. The excitation controller 24 outputs the driving signal CLS to cause the exciter 11 to generate and cut off a magnetostatic field. When an excitation coil is used for the exciter 11, the driving signal CLS is a voltage applied to the excitation coil. The excitation controller 24 may accordingly have a conventional circuit structure that enables application and cut-off of a voltage that drives the excitation coil. The sensor output controller 25 outputs the 4-bit sensor output selection signal SWS that successively selects one of the outputs of the sixteen magnetic sensors SR0 through SR15 included in the array sensor 12. The sensor power controller 26 outputs a sensor power switching signal PWS that starts and cuts off the supply of power to the Hall device in the magnetic sensor.

The signal processing unit 20b includes a wave-shaping unit 21 that modifies the detection signal SRS output from the array sensor 12 according to the input specification of an A-D converter 22, the A-D converter 22 that carries out A-D conversion of the input detection signal, a dual-port memory 23 that stores the digital data after the A-D conversion, an A-D converter controller 22a that regulates the timing of the A-D converter 22, and a memory controller 23a that controls write and read operations into and from the dual-port memory 23. In the case of the steel plate, significant effects of the eddy current loss on the transient variation of the detection signal SRS are observed within a time period of about 10 $\mu$s (3 $\mu$s to 6 $\mu$s on average) after the cut-off of the magnetostatic field. By taking into account this fact and the accuracy of data processing, it is desirable that the A-D converter 22 has the conversion rate of not lower than 4 Msps and the conversion accuracy of not less than 12 bits.

The data processing unit 30 processes the data that have been output from the sensor unit 10 shown in FIG. 7 and processed by the signal processing unit 20b, and determines the indentation diameter, the nugget diameter, and the joint diameter of the spot welded part. The data processing unit 30 is a computer system including a CPU and a main memory (not shown). The CPU executes computer programs stored in the main memory (storage medium) to implement a variety of data processing operations discussed later.

The measurement apparatus according to the present invention is not restricted to the above structure. In one modification of the structure shown in FIG. 7, for example, the sensor output selector 13 may be omitted and a plurality of signal processing units 20b corresponding to the number of the magnetic sensors may be provided, in order to enable the outputs of the respective magnetic sensors to be subjected to the signal processing in parallel.

C. Details of Measurement

The welding state of the spot welded part of the steel plate is examined by the following procedure. FIGS. 10(a) through 10(f) show the outputs of a magnetic sensor and results of data processing.

(1) Application and Cut-off of Magnetostatic Field

The driving signal CLS is output from the excitation controller 24 shown in FIG. 7 to control application and cut-off of a magnetostatic field in the excitation element 11. As shown in the graph of FIG. 10(a), the driving signal CLS is first made to be a high voltage signal $V_H$ in a time period $t_H$, in order to generate a magnetostatic field at a high speed. The driving signal CLS is then turned to be a low voltage signal $V_L$ in a time period $t_L$, in order to stabilize the magnetic flux density in the target body or the object to be measured. The driving signal CLS is cut off in a cut-off time period $t_R$, in order to cut the magnetostatic field off. The cut-off time period $t_R$ is preferably set equal to a value that enables the effect of the eddy current loss to be measured most significantly after the cut-off of the magnetostatic field. For example, in the case of the steel plate, the cut-off time period $t_R$ is in the range of about 3 $\mu$s to 6 $\mu$s.

(2) Measurement of Variation in Magnetism

Figure 11:
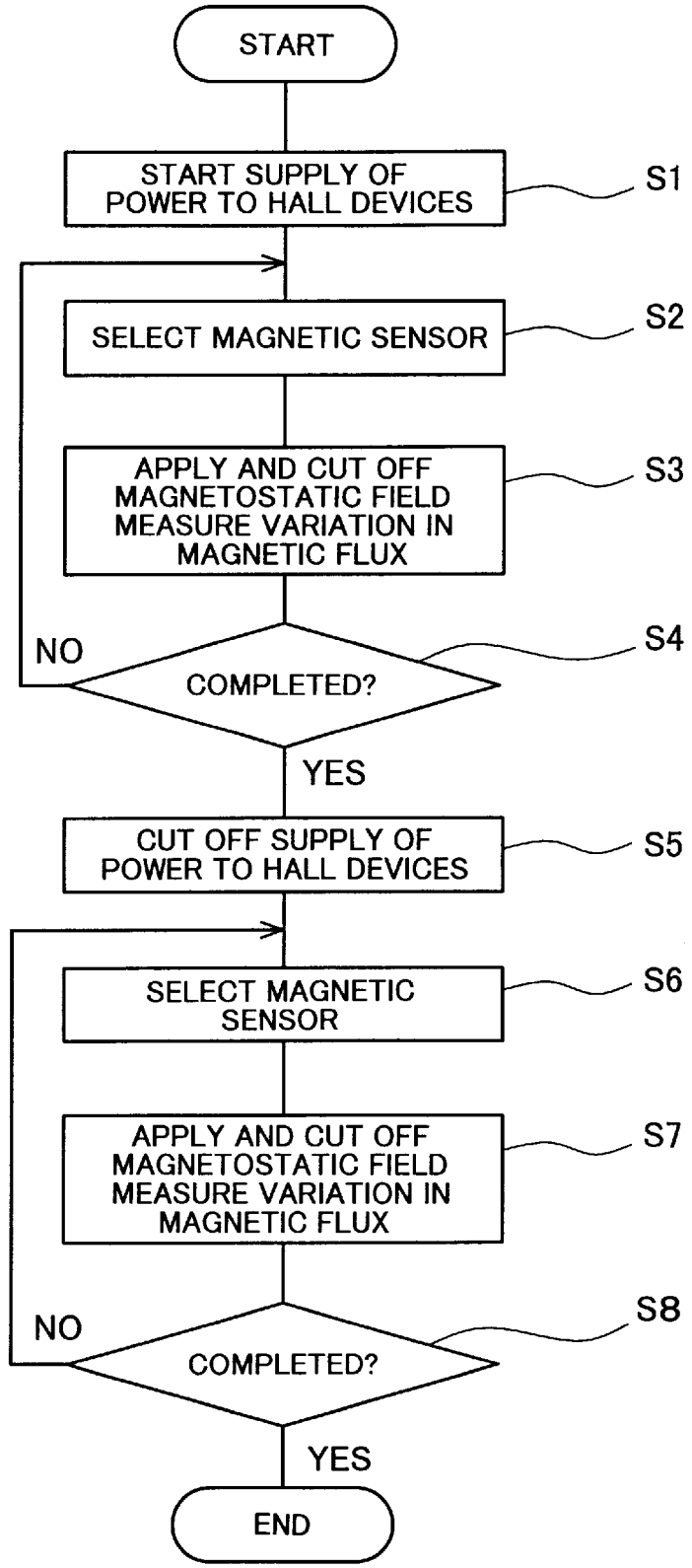
FIG. 11 is a flowchart showing a process of measuring a variation in magnetic flux.

In the course of the application and the cut-off of the magnetostatic field, the variation in magnetic flux in the vicinity of the target body is measured with the array sensor shown in FIG. 7. FIG. 11 is a flowchart showing a process of measuring a variation in magnetic flux. At step S1, the process starts a supply of power to the Hall devices included in the respective magnetic sensors. At subsequent step S2, the sensor output controller 25 outputs the sensor output selection signal SWS, and one of the magnetic sensors included in the array sensor 12 is selected in response to the sensor output selection signal SWS. The process then proceeds to step S3 to apply and cut off a magnetostatic field and measure the output of the selected magnetic sensor. The graph of FIG. 10(b) shows a variation in output of the magnetic sensor thus obtained. As described previously, while the Hall device is activated, the output SRS of the magnetic sensor is the sum of an output voltage $H_0$ of the Hall device and an output voltage $L_0$ of the loop coil. The observed detection signal SRS here is processed by the signal processing unit 20b. The variation in magnetic flux is measured successively with respect to the outputs of the Hall devices of all the magnetic sensors SR0 through SR15 through the repeated execution of steps S2 and S3. When the measurement is concluded for all the magnetic sensors SR0 through SR15 at step S4, the program proceeds to step S5, at which the sensor power controller 26 outputs the sensor power switching signal PWS, and the supply of power to the Hall devices of the respective magnetic sensors is cut off in response to the sensor power switching signal PWS. When the supply of power to the Hall device is cut off, the output of the array sensor 12 is equal to only the output of the loop coil. At subsequent step S6, the sensor output controller 25 outputs the sensor output selection signal SWS, and one of the magnetic sensors included in the array sensor 12 is selected in response to the sensor output selection signal SWS. The process then proceeds to step S7 to apply and cut off a magnetostatic field and measure the output of the selected magnetic sensor. The graph of FIG. 10(c) shows a variation in output of the magnetic sensor obtained at step S7, that is, the output $L_0$ of the loop coil. The observed detection signal SRS here is also processed by the signal processing unit 20b. The variation in magnetic flux is measured successively with respect to the outputs of the loop coils of all the magnetic sensors SR0 through SR15 through the repeated execution of steps S6 and S7. When the measurement is concluded for all the magnetic sensors SR0 through SR15 at step S8, the program exits from the routine of FIG. 11. In the signal processing unit 20b, the detection signals SRS are converted into 12-bit digital data at the conversion rate of 4 Msps by the A-D converter 22 and stored in the dual-port memory 23.

(3) Data Processing

After the measurement data are obtained according to the above procedure, the data processing unit 30 shown in FIG. 7 processes the data obtained for the respective magnetic sensors SR0 through SR15 and stored in the dual-port memory 23 and determines the required data to specify the welding state.

Figure 12:
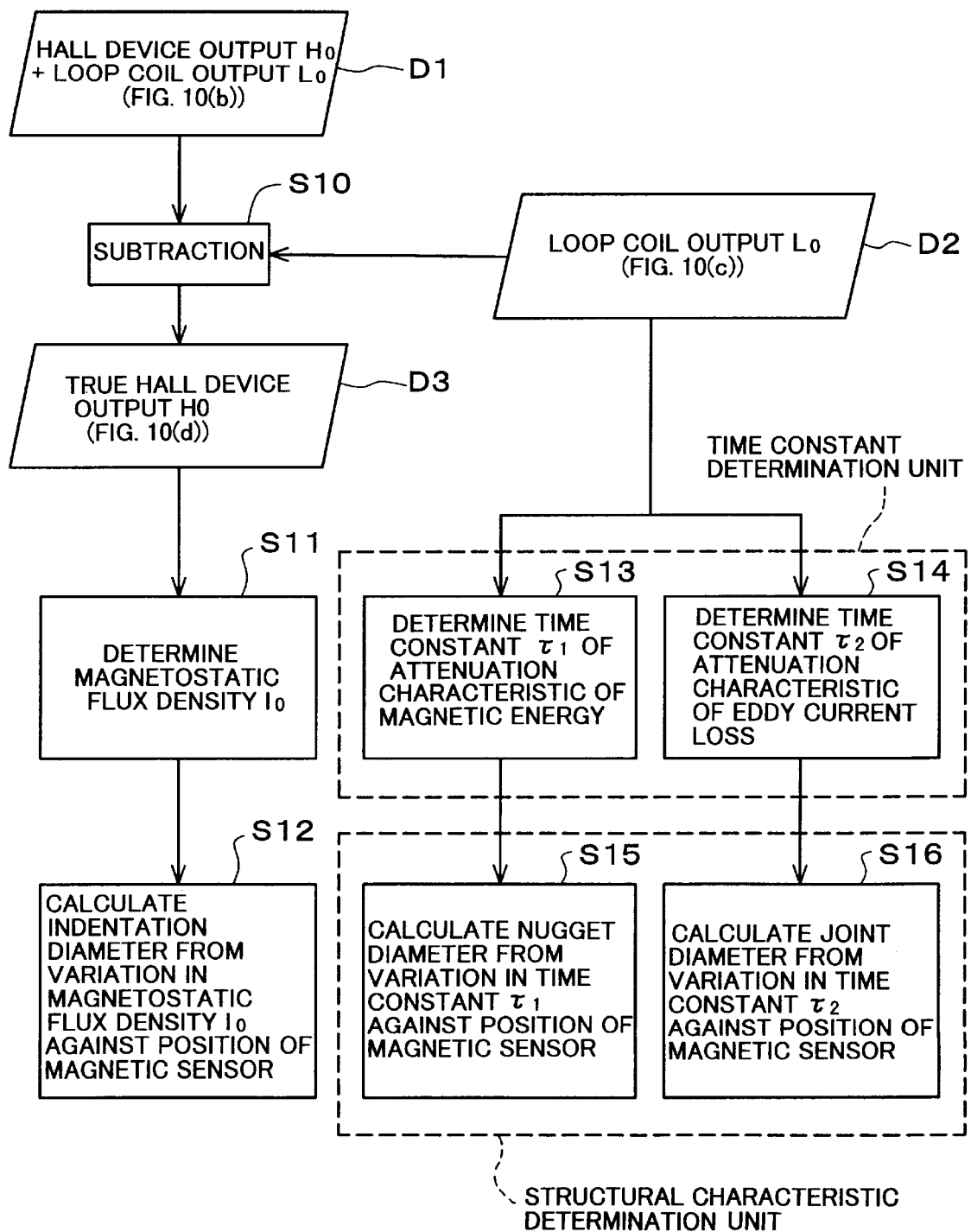
FIG. 12 is a flowchart showing a routine of data processing executed in the data processing unit.

FIG. 12 is a flowchart showing a routine of data processing executed in the data processing unit 30. At step S10, the process subtracts data D2 representing the variation in magnetic flux $L_0$ shown in FIG. 10(c) from data D1 representing the variation in magnetic flux ($H_0+L_0$) shown in FIG. 10(b) to obtain data D3 representing the true output $H_0$ of the Hall device shown in the graph of FIG. 10(d). At subsequent step S11, the process determines a magnetostatic flux density $I_0$ based on the output $H_0$ of the Hall device. When there is no variation in magnetic flux density, the output of the loop coil is equal to zero. In this case, the magnetostatic flux density $I_0$ can also be read from the initial sensor output shown in FIG. 10(b).

The output $L_0$ of the loop coil shown in FIG. 10(c) is proportional to the differential magnetic flux density given by Equation (6) discussed above, and is expressed as a composition of the attenuation characteristic of magnetic energy (the first term in the right-hand side) and the attenuation characteristic of eddy current loss (the second term in the left-hand side). At steps S13 and S14 in the flowchart of FIG. 12, the process analyzes the outputs $L_0$ of the loop coil and determines the time constant $\tau_1$ of the attenuation characteristic of magnetic energy and the time constant $\tau_2$ of the attenuation characteristic of eddy current loss. For example, the concrete procedure specifies a function representing a variation in output $L_0$ of the loop coil by the least squares method and compares the coefficients of the function with the coefficients in Taylor's expansion of Equation (6), so as to determine the time constants $\tau_1$ and $\tau_2$. This function corresponds to the time constant determination unit of the present invention. The graphs of FIGS. 10(e) and 10(f) respectively show the attenuation characteristics of magnetic energy and eddy current loss expressed by the time constants $\tau_1$ and $\tau_2$ thus obtained.

(4) Specification of Welding State

Referring back to the flowchart of FIG. 12, the process calculates the indentation diameter from the observed variation in magnetostatic flux density $I_0$ against the position of the magnetic sensor at step S12. The process also calculates the nugget diameter from the observed variation in time constant $\tau_1$ of the attenuation characteristic of magnetic energy against the position of the magnetic sensor at step S15. The process further calculates the joint diameter from the observed variation in time constant $\tau_2$ of the attenuation characteristic of eddy current loss against the position of the magnetic sensor at step S16. FIGS. 13(a) through 13(d) show a variation in magnetostatic flux density $I_0$ plotted against the position of the magnetic sensor, a variation in time constant $\tau_1$ plotted against the position of the magnetic sensor, and a variation in time constant $\tau_2$ plotted against the position of the magnetic sensor, which are obtained by measuring the magnetic flux in the spot welded part. As shown in FIGS. 13(a)–13(d), the magnetostatic flux density decreases in an indentation. The indentation diameter is thus determined by examining the point of change of the magnetostatic flux density. The time constant $\tau_1$ of the attenuation characteristic of magnetic energy decreases in a nugget. The nugget diameter is accordingly determined by examining the point of change of the time constant $\tau_1$. The time constant $\tau_2$ of the attenuation characteristic of eddy current loss increases at the positions of certain distances from the joint ends of the joint part. The joint diameter is thus determined by examining the point of change of the time constant $\tau_2$. The function of determining these structural characteristics corresponds to the structural characteristics specification unit of the present invention.

Figure 14:
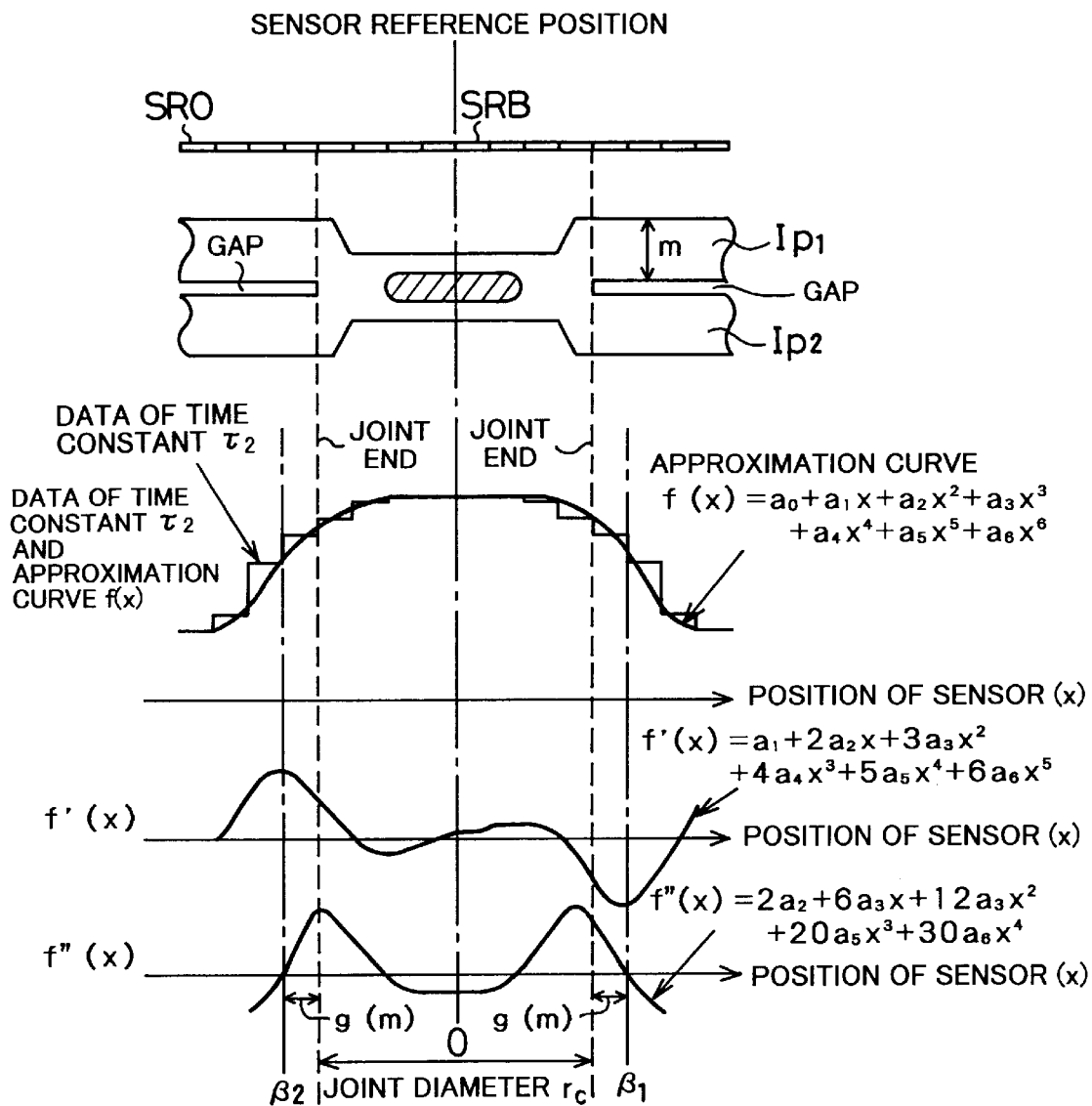
FIGS. 14(*a*) and 14(*b*) show one method of determining the joint diameter.
Figure 14:
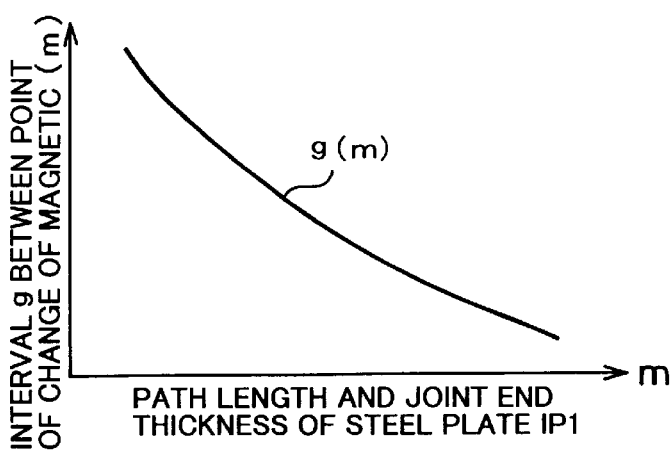

FIGS. 14(a) and 14(b) show one method of determining the joint diameter. The method first determines an approximation curve f(x) representing a variation in time constant $\tau_2$ against the position of the magnetic sensor by the least squares method as shown in FIG. 14(a). It is here preferable to use a sextic approximation equation or another higher-order approximation equation by taking into account the approximation accuracy of the approximation curve. The approximation equation is, however, not restricted to that of a sixth or higher order, but the 1pwer-order approximation equation may be used for the some of the waveforms to be approximated. Since the point of change in the waveform is either a maximum point of a minimum point of the slope of the waveform, the method calculates a first-order derivative f'(x) and a second-order derivative f"(x) of the approximation curve and determines roots $\beta_1$ and $\beta_2$ that show the maximum and the minimum in the first-order derivative f'(x) among the roots of the second-order derivative f"(x)=0. The time constant $\tau_2$ most abruptly varies at the positions of $\beta_1$ and $\beta_2$. The positions of $\beta_1$ and $\beta_2$ (see the curve of the second-order derivative f"(x) in FIG. 14(a)) accordingly represent the positions where the magnetic path of the magnetic flux is changed by the effect of the joint ends (that is, the points of change of the magnetic path length). The graph of FIG. 14(b) shows a variation in interval g(m) between the point of change of the magnetic path length and the joint end plotted against the thickness m of a steel plate $IP_1$. The curve representing the variation is obtained experimentally in advance. The joint diameter $\gamma_c$ is thus determined according to Equation (9) given below:

$$\gamma_c = \beta_1 - \beta_2 - 2g(m) \qquad (9)$$

Figure 13A:
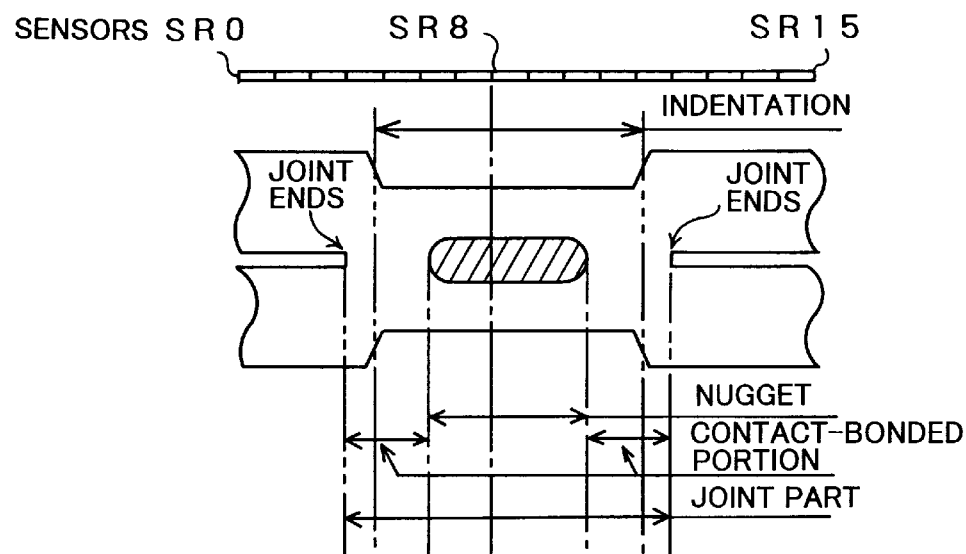
FIGS. 13(*a*) through 13(*d*) show a variation in magnetostatic flux density $I_0$ plotted against the position of the magnetic sensor, a variation in time constant $\tau_1$ plotted against the position of the magnetic sensor, and a variation in time constant $\tau_2$ plotted against the position of the magnetic sensor, which are obtained by measuring the magnetic flux in the spot welded part.
Figure 13B:
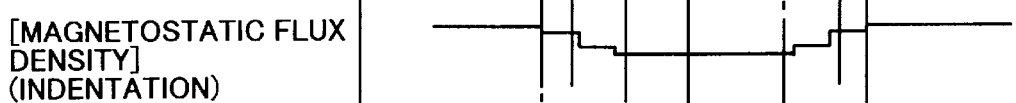
Figure 13C:
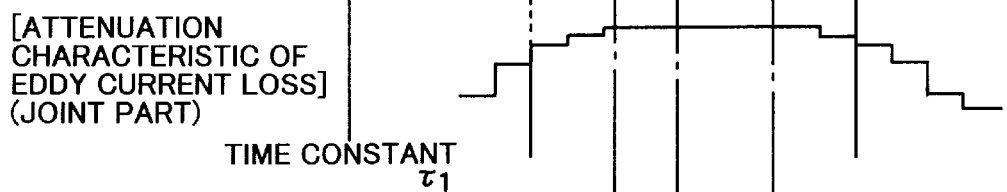
Figure 13D:
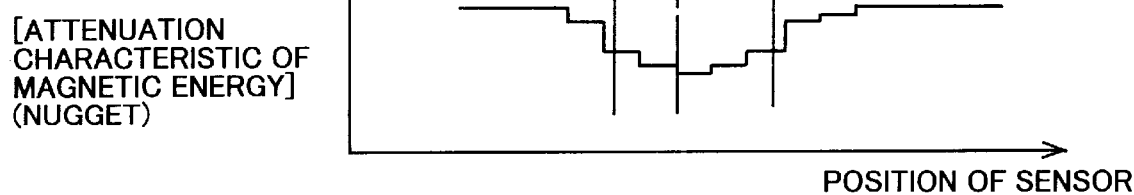

The indentation diameter is determined according to Equation (9) by analyzing the graph of FIG. 13(b) by the method of FIGS. 14(a) and 14(b) in the same manner as discussed above. The nugget diameter is also determined according to Equation (9) by analyzing the graph of FIG. 13(d) by the method of FIGS. 14(a) and 14(b). Since the indentation diameter and the nugget diameter can be obtained directly from the roots $\beta_1$ and $\beta_2$, g(m) in Equation (9) is set equal to zero.

D. Other Embodiments

The principle of the present invention is applicable to a variety of measurements discussed below, in addition to the measurement of the welding state of the spot welded part.

Figure 15A:
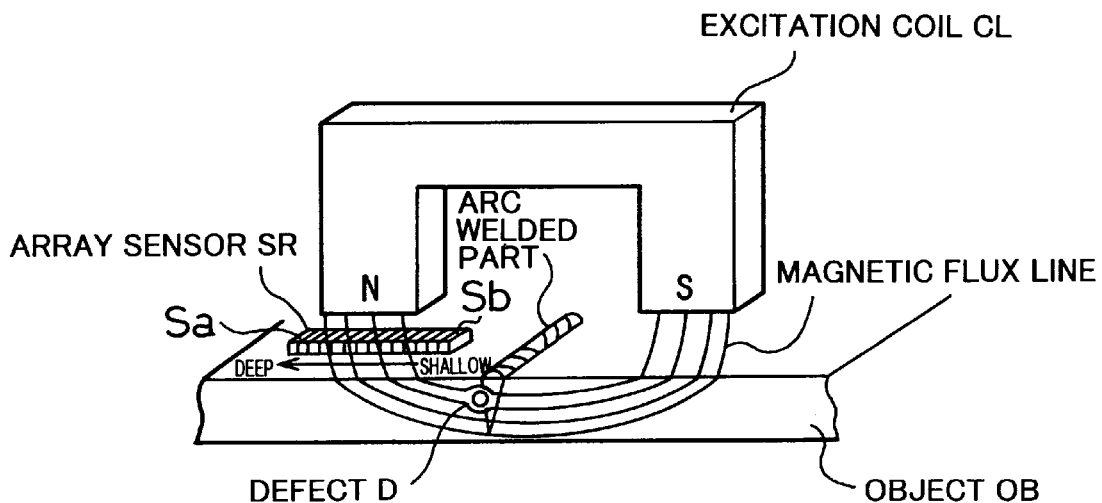
FIGS. 15(*a*) and 15(*b*) conceptually show a process of specifying the presence or absence of a defect in an object.
Figure 15B:
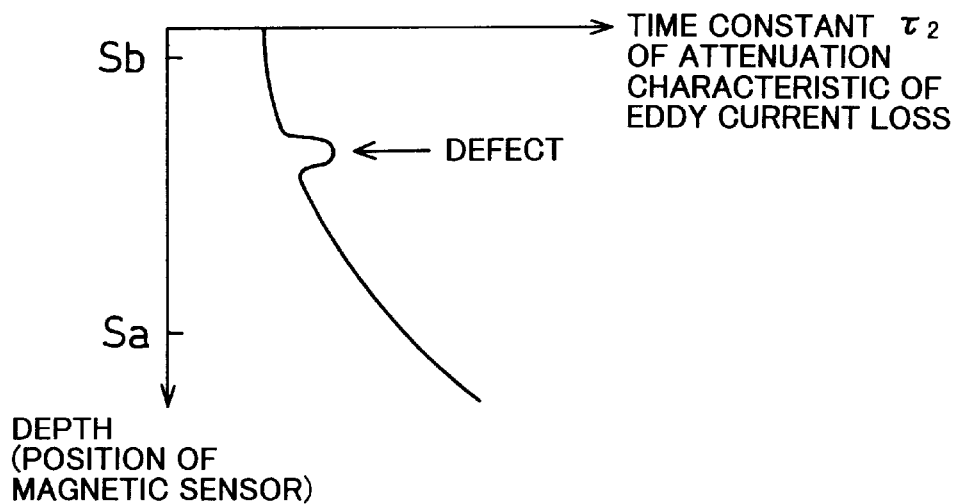

(1) When there is a defect inside a certain object (for example, a conductive magnetic body), the magnetic flux passing through the defect changes its magnetic path to go around the defect, like the change of the magnetic path in the vicinity of the joint end of the spot welded part. The change of the magnetic path is observed as an abrupt change of the time constant $\tau_2$ of the attenuation characteristic of eddy current loss in the course of variation in magnetism after the cut-off of the magnetostatic field. This arrangement specifies the presence or absence of a defect in the object. FIGS. 15(a) and 15(b) conceptually show a process of specifying the presence or absence of a defect in a target body or an object OB to be examined. In one example, a U-shaped excitation coil CL having the N magnetic pole and the S magnetic pole at both end projections thereof is located in such a manner that a defect D in the object OB is interposed between the N pole and the S pole of the excitation coil CL as shown in FIG. 15(a). An array sensor SR is then disposed immediately below the N pole and in the vicinity of the surface of the object OB, so that the magnetic sensors included in the array sensor SR are aligned in the direction connecting the N pole with the S pole. The method causes the excitation coil CL to apply a magnetostatic field to the object OB and measure a variation in magnetic flux in the vicinity of the object OB after the cut-off of the magnetostatic field with the array sensor SR. The magnetic flux lines running near a magnetic sensor Sb located on one end of the array sensor SR go through a shallower portion in the object OB, whereas the magnetic flux lines running near a magnetic sensor Sa located on the other end of the array sensor SR go through a deeper portion in the object OB. Namely the position of the magnetic sensor represents the depth in the object OB. The graph of FIG. 15(b) shows a variation in time constant $\tau_2$ of the attenuation characteristic of eddy current loss plotted against the position of the magnetic sensor. The sensor Sb measures a variation in magnetic flux passing through the shallower portion in the object OB, whereas the sensor Sa measures a variation in magnetic flux passing through the deeper portion in the object OB. When there is a defect at a position of a certain depth through where the magnetic flux passes, the time constant $\tau_2$ of the attenuation characteristic of eddy current loss has an abrupt change at the position of the depth as shown in FIG. 15(b). This arrangement thus determines the presence or absence of a defect and further determines the shape and the dimensions of the defect based on the abrupt change.

Figure 16A:
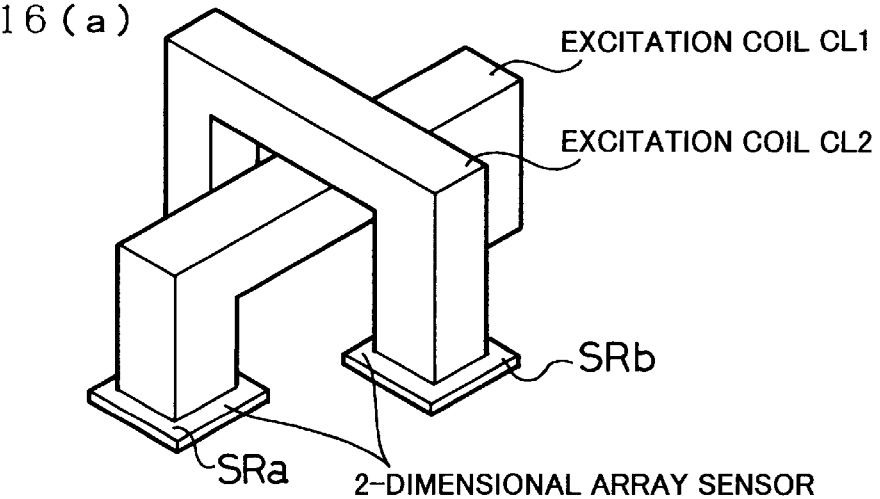
FIGS. 16(*a*) through 16(*c*) conceptually show a process of specifying the presence or absence of a defect in an object and further specifying the position of the defect.
Figure 16B:
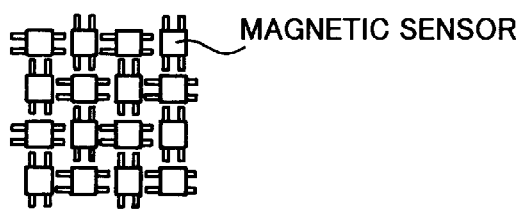
Figure 16C:
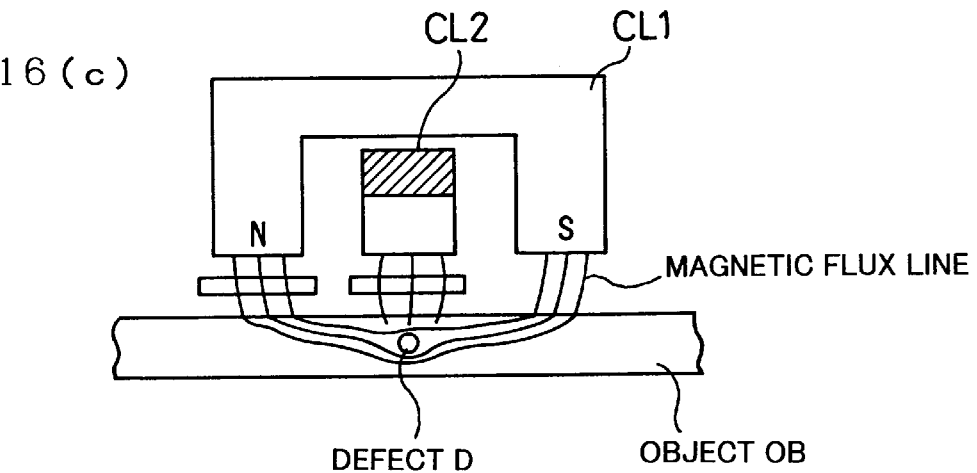

FIGS. 16(a) through 16(c) conceptually show a process of determining the presence or absence of a defect in an object and further determining the position of the defect. A pair of U-shaped excitation coils CL1 and CL2 are arranged to cross each other as shown in FIG. 16(a). Two-dimensional array sensors SRa and SRb are respectively disposed immediately below one magnetic pole of the excitation coils CL1 and CL2. Both the two-dimensional array sensors SRa and SRb include a plurality of magnetic sensors having a two-dimensional configuration shown in FIG. 16(b). When the measurement is carried out to find a defect D in an object OB as shown in FIG. 16(c), this arrangement enables a distribution of the defect D in the directions of the length, width, and depth to be measured and thereby determines the position, the shape, and the dimensions of the defect D.

Figure 17A:
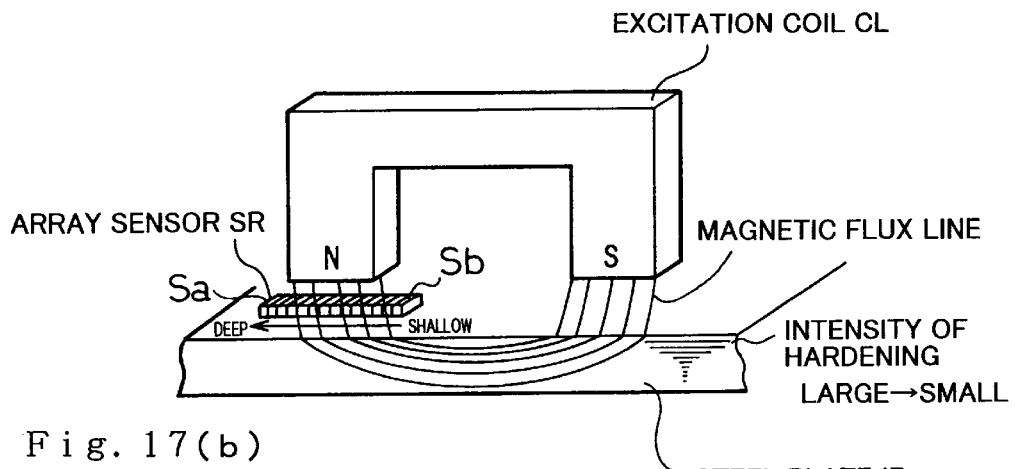
FIGS. 17(*a*) and 17(*b*) conceptually show a process of measuring the hardening state and intensity in a steel plate.
Figure 17B:
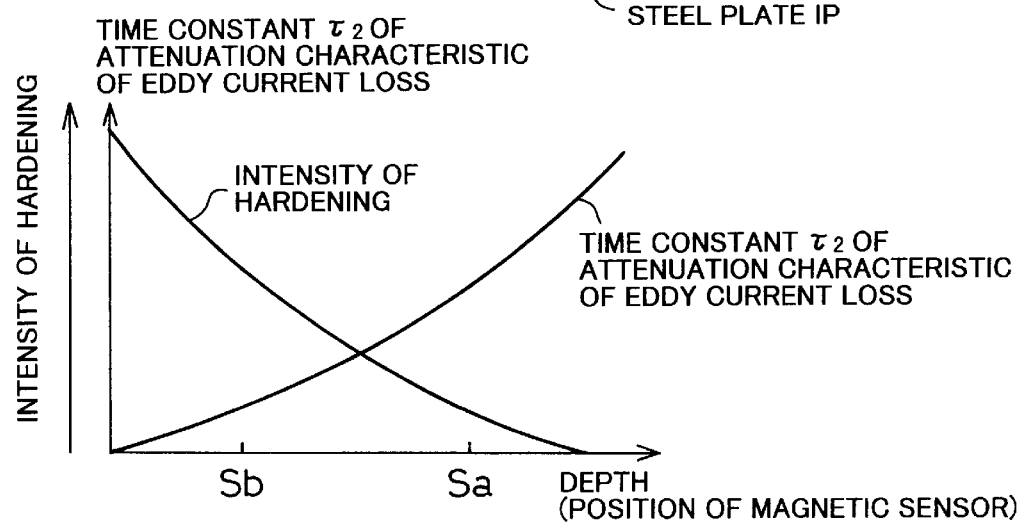

(2) A hardened part or a carburized layer of a steel plate IP have a higher resistivity and a smaller time constant $\tau_2$ of the attenuation characteristic of eddy current loss. This is clearly shown by Approximation Equation (4b) as discussed previously in the principle of measurement. The state (depth) and intensity of hardening and carburizing in the steel plate can thus be detected as a variation in time constant $\tau_2$ of the attenuation characteristic of eddy current loss in the course of a variation of the magnetism after the cut-off of the magnetostatic field. FIGS. 17(a) and 17(b) conceptually show a process of measuring the hardening state and intensity in a steel plate IP. In the measurement of FIG. 17(a), the excitation coil CL and the array sensor SR are arranged in the same manner as the measurement of FIG. 15(a). The process then measures a variation in time constant $\tau_2$ of the attenuation characteristic of eddy current loss in the course of a variation of the magnetism after the cut-off of the magnetostatic field. The graph of FIG. 17(b) shows a variation in time constant $\tau_2$ of the attenuation characteristic of eddy current loss plotted against the position of the magnetic sensor. A magnetic sensor Sb measures a change in the magnetic flux lines passing through a shallower portion in the object or the steel plate IP, whereas a magnetic sensor Sa measures a change in the magnetic flux lines passing through a deeper portion of the object. The hardening depth and intensity can thus be estimated from the observed variation in time constant $\tau_2$ of the attenuation characteristic of eddy current loss against the position of the magnetic sensor, as shown in the graph of FIG. 17(b).

Figure 18A:
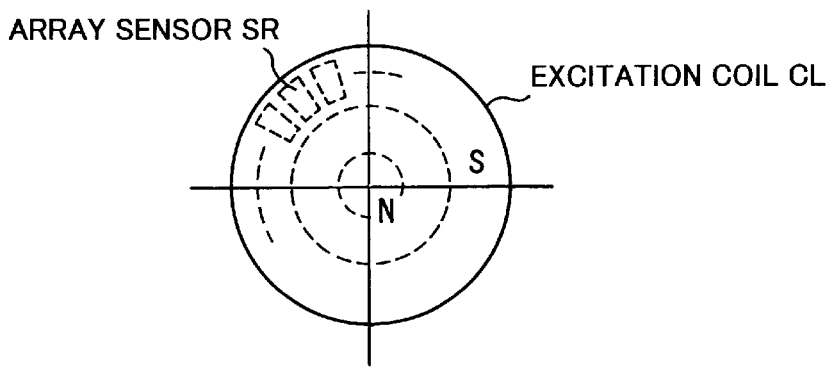
FIGS. 18(*a*) through 18(*c*) show a stress sensor to which the principle of measurement of the present invention is applied.
Figure 18B:
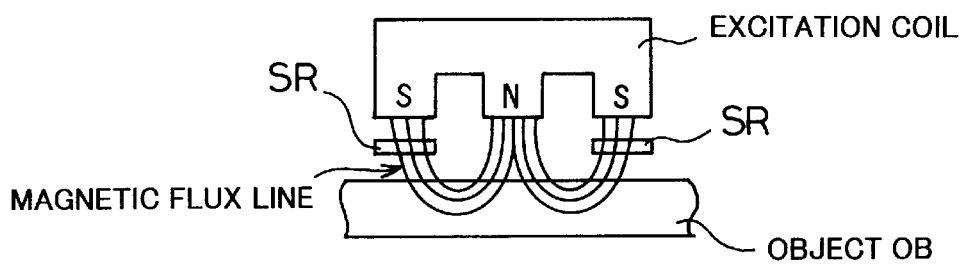
Figure 18C:
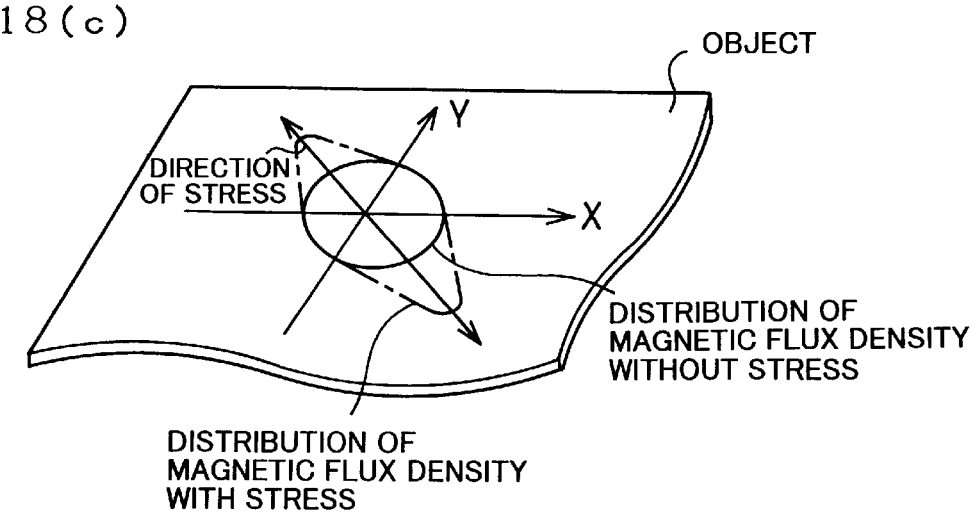
Figure 19:
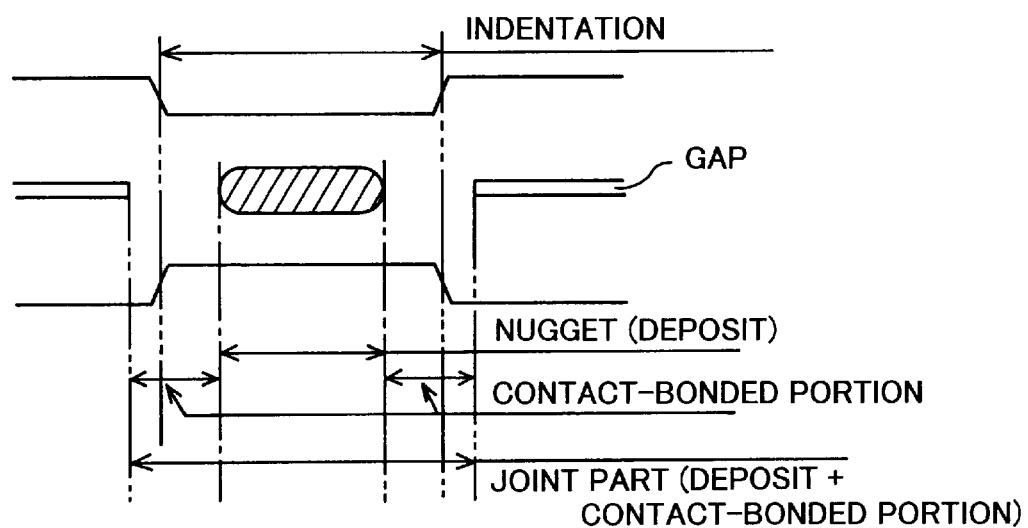
FIG. 19 shows the sectional structure of a spot welded part.

(3) FIGS. 18(a) through 18(c) show a stress sensor to which the principle of measurement of the present invention is applied. FIG. 18(a) is a top view illustrating the structure of an excitation coil CL that applies a magnetostatic field and an array sensor SR that measures a change in the magnetic flux lines. The excitation coil CL has a cylindrical outer shape and a multi-layered structure including a cylindrical N magnetic pole arranged on the center and lower portion and a ring-shaped S magnetic pole arranged on the circumferential and upper portion. The array sensor SR including a plurality of magnetic sensors aligned immediately below the S magnetic pole. FIG. 18(b) is a sectional view showing the state in which a magnetostatic field is applied to an object OB with the excitation coil CL and the array sensor SR shown in FIG. 18(a). The array sensor SR cuts off the magnetostatic field after magnetization of the object OB and measures a variation in magnetism in the vicinity of the object OB. When no stress is applied to the object OB, the observed magnetic flux density has a circular distribution as shown by the solid line in FIG. 18(c). When a stress is applied to the object OB in the direction of the arrow shown in FIG. 18(c), on the other hand, the observed magnetic flux density has a distortion as shown by the one-dot chain line. The permeability and the inductance change in the part receiving the stress, so that the time constant $\tau_2$ of the attenuation characteristic of eddy current loss varies. The stress applied to the object OR can thus be estimated from the variation in time constant $\tau_2$ of the attenuation characteristic of eddy current loss that is observed by the array sensor SR arranged immediately below the excitation coil CL in the course of the application of the stress.

The present invention is not restricted to the above embodiments or their modifications, but there may be many other modifications, changes, and alterations without departing from the scope or spirit of the main characteristics of the present invention.

What is claimed is:

1. A method of examining an internal structure of a target magnetic body, said method comprising the steps of:
    (a) applying a magnetostatic field to a target magnetic body to magnetize the target magnetic body;
    (b) cutting the magnetostatic field off and subsequently measuring a transient variation in a differential magnetic flux density at a plurality of position in the vicinity of the target magnetic body, the differential magnetic flux density being a differentiation of a magnetic flux density with respect to time;
    (c) determining a time constant of the transient variation in the differential magnetic flux density at the plurality of positions; and
    (d) determining a specific characteristic value relating to the internal structure of the target magnetic body, based on a distribution of the time constant over the plurality of positions.

2. A method in accordance with claim 1, wherein said step (c) includes the step of:
    assuming the transient variation in the differential magnetic flux density to be a combination of a transient variation in a first differential magnetic flux density corresponding to an attenuation of a first magnetic flux density caused by the magnetostatic field and a transient variation in a second differential magnetic flux density corresponding to an attenuation of a second magnetic flux density caused by an eddy current, which is induced by the attenuation of the first magnetic flux density, and determining at least one of a first time constant defining the transient variation in the first differential magnetic flux density and a second time constant defining the transient variation in the second differential magnetic flux density.

3. A method in accordance with claim 2, wherein the target magnetic body is a plate assembly obtained by joining two metal plates by spot welding, and
    wherein said step (d) includes the step of:
    determining a shape of a nugget portion of a spot welded part, based on a distribution of the first time constant.

4. A method in accordance with claim 2, wherein the target magnetic body is a plate assembly obtained by joining two metal plates by spot welding, and wherein said step (d) includes the step of:

determining a shape of a joint portion of a spot welded part, based on a distribution of the second time constant.

5. An apparatus for examining an internal structure of a target magnetic body, comprising:

a magnetostatic field application unit that applies a magnetostatic field to a target magnetic body to magnetize the target magnetic body;

a measurement unit that cuts the magnetostatic field off and subsequently measures a transient variation in a differential magnetic flux density at a plurality of positions in the vicinity of the target magnetic body, the differential magnetic flux density being a differentiation of a magnetic flux density with respect to time;

a time constant determination unit that determines a time constant of the transient variation in the differential magnetic flux density at the plurality of positions; and a structural characteristic determination unit that determines a specific characteristic value relating to the internal structure of the target magnetic body, based on a distribution of the time constant over the plurality of positions.

6. An apparatus in accordance with claim 5, wherein said time constant determination unit assumes the transient variation in the differential magnetic flux density to be a combination of a transient variation in a first differential magnetic flux density corresponding to an attenuation of a first magnetic flux density caused by the magnetostatic field and a transient variation in a second differential magnetic flux density corresponding to an attenuation of a second magnetic flux density caused by an eddy current, which is induced by the attenuation of the first magnetic flux density, and determines at least one of a first time constant defining the transient variation in the first differential magnetic flux density and a second time constant defining the transient variation in the second differential magnetic flux density.

7. An apparatus in accordance with claim 6, wherein the target magnetic body is a plate assembly obtained by joining two metal plates by spot welding, and wherein said structural characteristic determination unit determines a shape of a nugget portion of a spot welded part, based on a distribution of the first time constant.

8. An apparatus in accordance with claim 6, wherein the target magnetic body is a plate assembly obtained by joining two metal plates by spot welding, and wherein said structural characteristic determination unit determines a shape of a joint portion of a spot welded part, based on a distribution of the second time constant.

9. The method, as recited in claim 1, wherein the cutting the magnetostatic field and subsequently measuring, comprises using a loop coil for the measuring.

10. The method, as recited in claim 9, wherein the cutting the magnetostatic field and subsequently measuring, further comprises using a hall device electrically connected to the loop coil.

11. The apparatus, as recited in claim 5, wherein the measurement unit, comprises a loop coil.

12. The apparatus, as recited in claim 11, wherein the measurement unit, further comprises a hall device.

13. The apparatus, as recited in claim 12, wherein the loop coil is electrically connected in series with the hall device.

14. A method of examining an internal structure of a target magnetic body, said method comprising the steps of:

(a) applying a first magnetostatic field to a target magnetic body to magnetize the target magnetic body;

(b) cutting the first magnetostatic field;

(c) using a first coil loop to provide a first magnetic flux density measurement at a first location;

(d) determining a first time constant at the first location based on the first magnetic flux density; and (e) determining a specific characteristic value relating to the internal structure of the target magnetic body is further based on the first time constant at the first location.

15. The method, as recited in claim 14, further comprising the steps of:

(a) applying a second magnetostatic field to the target magnetic body;

(b) cutting the second magnetostatic field;

(c) using a second coil loop to provide a first magnetic flux density measurement at a second location; and (d) determining a first time constant at the second location based on the first magnetic flux density at the second location, wherein the determining a specific characteristic value relating to the target magnetic body is based on the first time constant at the second location.

16. The method, as recited in claim 15, further comprising the steps of:

(a) applying a third magnetostatic field to the target magnetic body;

(b) cutting the third magnetostatic field;

(c) using the first coil loop and a first hall device to provide a second magnetic flux density measurement at the first location;

(d) applying a fourth magnetostatic field to the target magnetic body;

(e) cutting the fourth magnetostatic field; and (f) using the second coil loop and a second hall device to provide a second magnetic flux density measurement at the second location.

17. The method, as recited in claim 16, further comprising the steps of:

(a) determining a second time constant at the first location; and (b) determining a second time constant at the second location, wherein the determining a specific characteristic value relating to the target magnetic body is further based on the second time constant at the first location and the second time constant at the second location.

* * * * *